(12) United States Patent
Gray

(10) Patent No.: US 6,749,596 B2
(45) Date of Patent: Jun. 15, 2004

(54) USE OF A POLARIZING FIELD TO MODIFY THE EFFICACY OF A BIOACTIVE AGENT

(76) Inventor: James R. Gray, 8816 Westwood, Little Rock, AR (US) 72204

(*) Notice: Subject to any disclaimer, the term of this patent is extended or adjusted under 35 U.S.C. 154(b) by 0 days.

(21) Appl. No.: 10/196,467

(22) Filed: Jul. 15, 2002

(65) Prior Publication Data

US 2002/0193832 A1 Dec. 19, 2002

Related U.S. Application Data

(63) Continuation of application No. 09/000,196, filed as application No. PCT/US96/12361 on Jul. 26, 1996, now Pat. No. 6,447,499.
(60) Provisional application No. 60/001,719, filed on Jul. 28, 1995.

(51) Int. Cl.[7] .............................................. A61M 31/00
(52) U.S. Cl. ............................. 604/500; 604/20; 600/9
(58) Field of Search .......................... 604/522, 20, 22, 604/500; 424/450; 600/9, 13, 14

(56) References Cited

U.S. PATENT DOCUMENTS

| | | |
|---|---|---|
| 3,368,155 A | 2/1968 | Priore |
| 4,094,322 A | 6/1978 | Hara |
| 4,106,488 A | 8/1978 | Gordon |
| 4,141,359 A | 2/1979 | Jacobsen et al. |
| 4,269,826 A | 5/1981 | Zimmermann et al. |
| 4,303,636 A | 12/1981 | Gordon |
| 4,323,056 A | 4/1982 | Borrelli et al. |
| 4,359,453 A | 11/1982 | Gordon |
| 4,587,957 A | 5/1986 | Castel |
| 4,683,873 A | 8/1987 | Cadossi et al. |
| 4,829,984 A | 5/1989 | Gordon |
| 4,950,221 A | 8/1990 | Gordon |
| 4,993,413 A | 2/1991 | McLeod et al. |
| 5,224,927 A | 7/1993 | Tapper |
| 5,281,196 A | 1/1994 | Sultenfuss |
| 5,304,111 A | 4/1994 | Mitsuno et al. |
| 5,336,168 A | 8/1994 | Sibalis |
| 5,342,410 A | 8/1994 | Braverman |
| 5,397,338 A | 3/1995 | Grey et al. |
| 5,529,568 A | 6/1996 | Rayman |
| 5,647,361 A | 7/1997 | Damadian |
| 5,707,334 A | 1/1998 | Young |
| 5,722,409 A | 3/1998 | Kuhara et al. |

Primary Examiner—Mark Bockelman
(74) Attorney, Agent, or Firm—Mark Rogers; Gary N. Speed

(57) ABSTRACT

A bioactive agent is administered to a patient, and the efficacy of the bioactive agent is modified by exposing the patient to a polarizing field. The bioactive agent may be a chemotherapeutic agent administered to a patient with cancer, and the polarizing field may be an electric field and/or a magnetic field. The direction and/or strength of the polarizing field may be changed during treatment to promote the opportunity for enhanced therapeutic interaction between the bioactive agent and the field.

27 Claims, 4 Drawing Sheets

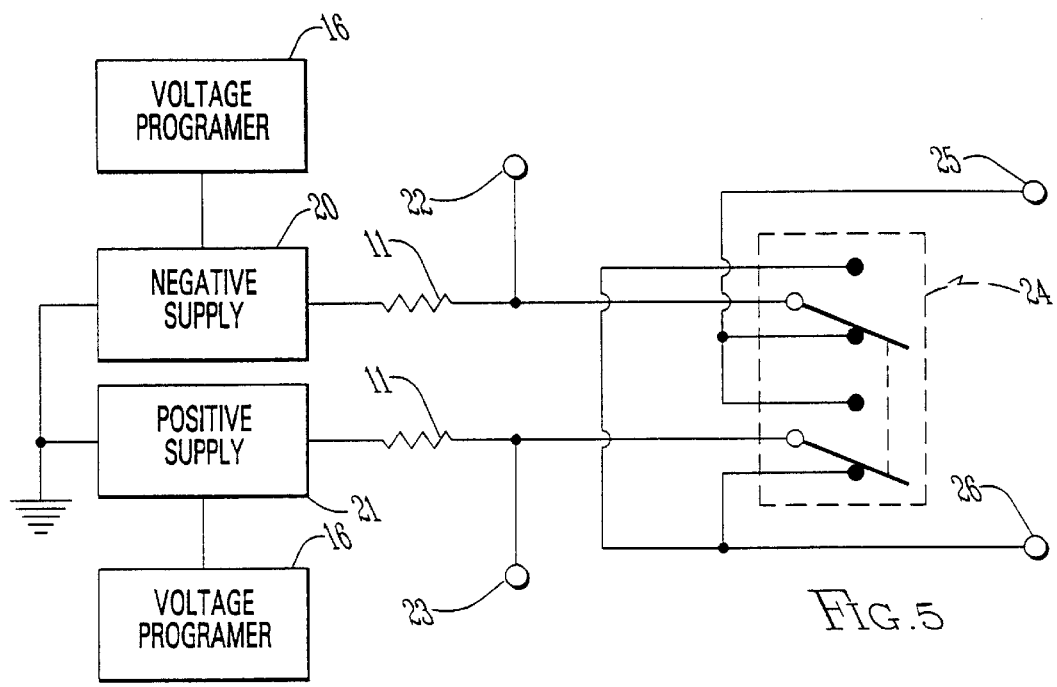
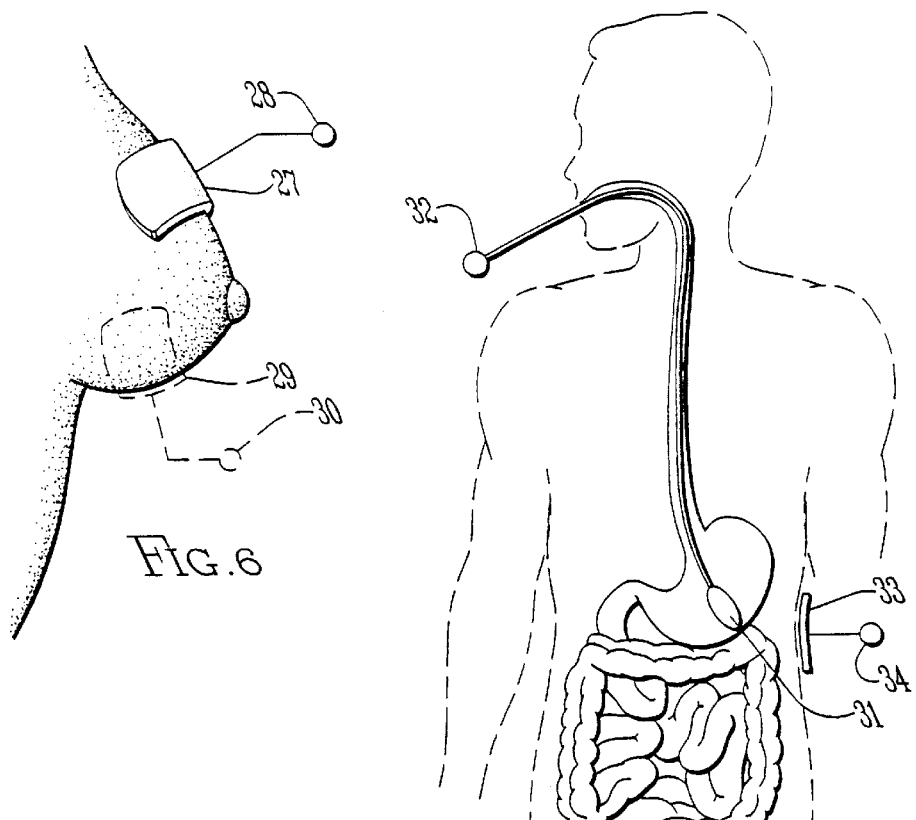

USE OF A POLARIZING FIELD TO MODIFY THE EFFICACY OF A BIOACTIVE AGENT

This application is a continuation application of and claims priority from U.S. patent application Ser. No. 09/000,196, filed on Jul. 27, 1998, now U.S. Pat No. 6,447,499 which is a 371 of PCT/US96/12361 filed on Jul. 26, 1996, which claims priority from U.S. Provisional Patent Application Serial No. 60/001,719, filed on Jul. 28, 1995.

TECHNICAL FIELD

The invention relates to the electrophysiology of the human body. More specifically, the invention provides methods of altering normal charge distribution within selected areas of the body to increase the effectiveness of bioactive agents such as drugs in these areas.

BACKGROUND ART

Modern medical practice includes the application of electromotive force, defined by the *Handbook of Chemistry and Physics*, 39th Edition, as "that which causes a flow of current", to the body in several beneficial techniques. For example, pharmacological agents are delivered to, or released at, target sites within the body through the use of current flow, either between electrodes or induced by oscillating or pulsing electric or magnetic fields which alternately push and pull electrons within the body structure. Balkiston's Gould Medical Dictionary (McGraw-Hill) defines these techniques as:

Iontophoresis: a method of inducing therapeutic particles into skin or other tissue by means of electric current.

Electrophoresis: the migration of charged colloidal particles through the medium in which they are disbursed when placed under the influence of an applied electric potential.

Electroosmosis: the movement of a conducting liquid through a permeable membrane under the influence of a potential gradient, thought to be caused by the opposite electrification of the membrane and liquid.

U.S. Pat. Nos. 4,141,359 and 5,336,168 show representative methods of these technologies.

In another medical use of electromotive force, direct or induced current flow is used to promote bone healing. U.S. Pat. Nos. 4,683,873 and 4,993,413 show representative methods of this technology.

In still another medical use of electromotive force, direct or induced current flow is used for "electrostimulation" of nerves to mask pain. U.S. Pat. Nos. 5,342,410 and 5,397,338 show representative methods of this technology.

The foregoing uses of electromotive force in medicine all involve a flow of current, or continuous movement of charge carriers (i.e., electrons or ions) through a conductive medium under the influence of an electric field that is maintained in the medium by contact with a power source. Unless an electric field within a conductor is maintained by a power source, however, the field and thus also the current will drop to zero regardless of the field outside the conductor. This is a well known and accepted tenet of basic physics. In regard to conductive biological systems, some researchers in the field have predicted, on a theoretical level, that an external electric field with no conductive connection to the body is reduced to such a degree inward of the surface of a human body that it has been commonly believed that an external electric field alone could have little effect inside the body. For example, one researcher has used Maxwell's equations with certain boundary conditions to mathematically predict that a static electric field passing inside a living organism is rendered one trillion times smaller inside the organism than the same field outside the organism. Also, the same equations have been employed to support a prediction that the electric field portion of a 60 Hertz electromagnetic field is rendered 40 billion times smaller inside a living organism than the same field outside the organism (*CRC Handbook of Biological Effects of Electromagnetic Fields*, CRC Press, pages 5–9, 1986).

As a result of this common belief concerning abrupt reduction of an external electric field at the surface of a living organism, the question of whether such a field may have biological effects on living organisms has received little attention.

A magnetic field, on the other hand, is able to penetrate into a conductor. Unlike external electric fields, magnetic fields have a role in the modern practice of medicine. For example, large magnets are used in nuclear magnetic resonance imaging systems.

A magnetic field can have biological consequences. Researchers have reported that a magnetic field can alter the growth of bacteria and yeasts. Researchers have also reported that a magnetic field can alter enzyme activity in vitro, particularly if the field is non-uniform. Furthermore, researchers have reported that a magnetic field reduces the ability of protozoa to survive exposure to a toxic substance. See the *CRC Handbook of Biological Effects of Electromagnetic Fields*, supra, at pages 173–175.

The prior art does not contemplate the use of static electric or static magnetic fields to increase the effectiveness of bioactive agents by altering the receptivity or susceptibility of cells, or other therapeutic targets such as bacteria or viruses for example, to such agents. These methods form the basis of the invention.

DISCLOSURE OF THE INVENTION

It is now recognized that every action in every living organism, including the human body, results from electric charges and their attendant electric fields. Each of the approximately seventy-five trillion cells in a human body utilizes specific patterns of electric charges to create specific patterns and strengths of electric fields on, within, and around the cell membranes and interior components to carry out the various processes required to maintain life. Abnormal charge distributions can lead to an inability to properly carry out normal processes and result in maladies ranging from aches and pains to serious disease. Such maladies, and even a genetic susceptibility to such maladies, shall be referred to herein as "disease conditions".

The drugs and other bioactive agents that are administered to treat such maladies have molecules with a specific electron arrangement which provides a specific electric field. Organic materials such as cells in the human body likewise have chemical constituents with specific electron and electric field arrangements, as do pathogens and toxins. The reason a particular bioactive agent is effective in treating a particular disease is generally that the specific electron and electric field arrangement exhibited by the bioactive agent interacts, in a complimentary fashion, with the specific electron and electric field arrangement exhibited by a site on a therapeutic target, such as human cells, enzymes, bacteria, and so forth. This interaction alters the nature of the target in a manner that is beneficial to the patient. For example, a bioactive agent may have an electrical configuration which interacts with that at some location of a human cell to cause the agent to accumulate near, or attach to, a specific receptor on or in the cell. This, at least temporarily, beneficially alters the cell, or the cell's operation, or aids the cell in carrying out normal processes. This dependence on specific electron and field strength patterns is the reason bioactive agents are effective against some maladies and not others. This is also the reason some agents are only marginally effective, i.e., the electron pattern and resulting field strength of the agent's molecules are not quite right for optimum attraction of, and connection with, a therapeutic target giving the desired result. It is almost universally desirable to increase the effectiveness, or increase the range of effects, of the bioactive agents in the medical pharmacopoeia.

The inventor has discovered that exposing the body, or specific desired areas of the body, to a static electric field or to a static magnetic field can significantly increase the effect of some bioactive agents on the body. Presumably these fields act to slightly alter or strengthen the electric charge distribution pattern near, on, or within the exposed body cells, and thus increase the receptivity or susceptibility of the cells to reaction with the bioactive agent. Also, there is reason to believe that using static electric or static magnetic force fields to alter the normal electric charge distribution near, on, or within the exposed cells may in addition cause the cells to prematurely initiate some of their normal metabolic operations and thus place them in a condition which increases their receptivity or susceptibility to applied bioactive agents.

The term "static electric field" as used herein is intended to mean fields from an electrical potential which maintain the same polarity over a period of time of at least 1 second, but more commonly over minutes or hours. The term "static magnetic field" as used herein is intended to mean fields from a magnetic element which maintain the same polarity over a period of time of at least 1 second, but more commonly over minutes or hours.

Static electric and static magnetic fields will occasionally be referred to collectively herein as "polarizing fields." This nomenclature is believed to be appropriate since a nonpolar particle such as a molecule in an electric field may become polarized by induction, and the dipole moment or degree of polarization of an inherently polarized particle is modified by a static electric field. The mere presence of a static magnetic field does not induce or modify polarization, but a static magnetic field is nevertheless appropriately characterized as a polarizing field in the context of the invention since the degree of polarization of an inherently polarized particle which moves with respect to a magnetic field is modified by the magnetic field. For a living body, such movement is to be expected.

According to the invention, a bioactive agent is administered to a patient and the patient's body or a target region thereof is exposed to a polarizing field without producing current flow or heat, as would occur if the patient's body were made to be part of an electric circuit, or exposed to moving magnetic fields, as in the prior art. Instead, the polarizing field is applied to achieve a polarizing effect within the tissue, creating dipoles from particles such as atoms, ions, or molecules in, on, or near the components of the tissue, or modifying the charge distribution of such particles if they are inherently polarized, to achieve enhanced reaction with a desired bioactive agent. Depending on the components of the tissue, the polarizing field applied, and the bioactive agent, the individual components and/or bioactive agent may be influenced in a number of ways, for example they may:

shift their electron distribution to favor reaction.

shift their electron distribution to create charge gradients favoring attraction of, and reaction between, the components and bioactive agents.

rotate to expose a surface favoring reaction.

move to a location (within the cell membrane for example) favoring reaction.

prematurely initiate a normal activity or process of the cells or other components which favors reaction with the desired bioactive agent.

A polarizing field is applied with the polarizing force in one direction long enough to achieve any, or any combination of, the above actions. Typically the polarizing force direction of the applied field will be maintained for at least numbers of seconds, but most often for numbers of minutes or hours, or continuously, during the treatment period. The force direction may also be periodically changed to provide additional opportunities for cellular reaction.

The steps in using the invention may vary to meet the requirements of specific bioactive agents, or specific locations of a patient's body. Most often, the steps will include:

1. Administering the desired bioactive agent or agents to the patient through any medically approved route.
2. While the agent is present in the body (even as the agent is being administered, if desired) exposing at least a target region of the body to a polarizing field.
3. Continuing the polarizing field exposure for a length of time based on the active life of the bioactive agent, or at least a portion of the active life, such as half-life, for example.
4. Discontinuing the exposure to the polarizing field after the desired effect has occurred, or at a point based on the active life of the bioactive agent.

It is an object of the invention to increase the effectiveness of a bioactive agent or agents administered to the body by exposing the whole body, or a selected target region of the body, to a nonuniform, or to a relatively uniform, polarizing static electric and/or static magnetic field.

Another object of the invention is to increase the effectiveness of a bioactive agent or agents administered to the body by exposing all of the body, or a selected target region of the body, to a nonuniform, or to a relatively uniform, polarizing static electric and/or static magnetic field long enough to influence charge distribution near, on, or within the exposed cells to increase the receptivity or susceptibility of the cells to interaction with the bioactive agent by increasing attraction of the agent to locations on and/or in the cells, and/or by initiating or preventing a metabolic process of the cells in the presence of the agent.

Another object of the invention is to increase the effectiveness of a bioactive agent or agents administered to the body by exposing all of the body, or a selected target region of the body, to a nonuniform, or to a relatively uniform, polarizing static electric and/or static magnetic field, long enough to influence charge distribution near, on, or within exposed cells to increase the receptivity or susceptibility, or initiate or prevent metabolic processes, of the cells so as to optimize interaction with the bioactive agent at some location of the cells, then changing the direction of the polarizing field one or more times to create the same conditions and reactions at other locations of the cells.

Another object of the invention is to increase the effectiveness of a bioactive agent or agents administered to the body by exposing all of the body, or a selected target region of the body, to a nonuniform, or to a relatively uniform, polarizing static electric and/or static magnetic field with sufficient amplitude (strength) to influence the charge distribution near, on, or within exposed cells so as to increase the receptivity or susceptibility of the cells to interaction with the bioactive agent by increasing the attraction of the agent to locations of the cells and/or by initiating or preventing a metabolic process of the cells in the presence of the agent.

Another object of the invention is to increase the effectiveness of a bioactive agent or agents administered to the body by exposing all of the body, or a selected target region of the body, to a nonuniform, or to a relatively uniform, polarizing static electric and/or static magnetic field of one amplitude (strength) to influence the charge distribution near, on, or within exposed cells to a certain degree, and by then increasing and/or decreasing the amplitude one or more times to influence the charge distribution near, on, or within exposed cells to another degree, so as to increase the receptivity or susceptibility of the cells to interaction with the bioactive agent by increasing attraction of the agent to locations of the cells and/or by initiating or preventing metabolic processes of the cells in the presence of the agent.

It is another object of the invention to increase the effectiveness of a bioactive agent or agents administered to the body by exposing all of the body, or a selected target region of the body, to a nonuniform, or to a relatively uniform, polarizing static electric and/or static magnetic field creating charge gradients near, on, or within exposed cells to increase the receptivity or susceptibility of the cells to interaction with the bioactive agent by increasing the attraction of the agent to locations of the cells and/or by initiating or preventing a metabolic process of the cells in the presence of the agent because of a particular charge level so created at some location on, near, or within the cells.

It is another object of the invention to use any combinations of the methods of the above noted objects to increase the effectiveness of any bioactive agent or agents administered to the body in the presence of a polarizing field.

These objects, as well as other objects, which will become apparent in the following discussion, may be selectively achieved singularly or in any combination, and the invention may be practiced with one or combinations of bioactive agents. The result is a highly desirable increase in action of the bioactive agent, or agents, which can increase their therapeutic potency, even to the point of requiring less bioactive agent if desired. Also, if desired, the increased action of the bioactive agent may be restricted to only certain areas of the body, thus reducing what may be undesired action of the agent or agents in or on other areas of the body. In addition, the increased action of the bioactive agent may result in agents which were formerly only marginally effective becoming effective enough for beneficial use.

BRIEF DESCRIPTION OF DRAWINGS

FIG. 5 is a block diagram of yet another embodiment of a power supply system;

FIG. 6 is a side elevational view showing one embodiment of a treatment element and an optional additional treatment element for exposing a target region of the body to an electric field;

FIG. 7 is a elevational view showing an embodiment of an insulated conductive element inside a body cavity;

MODES FOR CARRYING OUT THE INVENTION

Figure 1:
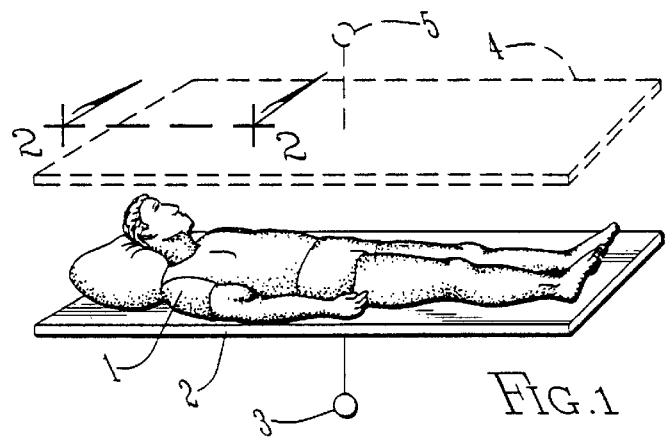
FIG. 1 is a perspective view of a patient undergoing total body exposure to a static electric field after receiving a bioactive agent, in accordance with one embodiment of the invention.

The invention arises from the inventor's discovery that the efficacy of a bioactive agent which has been administered to a mammal can be modified by exposing the mammal to a polarizing field (that is, a static electric field or a static magnetic field, or both). This discovery is based on experiments with mice which the inventor has conducted. But before either the experiments or specific practical embodiments of the invention are described, a theoretical discussion will be offered in an effort to aid in understanding and practicing the invention. However, it must be recognized that our knowledge of cellular operation at the molecular level is incomplete. For example, it is not currently possible to accurately predict the effect of chemical agents on cells, so mass screenings are used to identify drug candidates. Also, it is not currently understood how most cell processes, including major processes such as differentiation or division, are initiated or controlled. The discussions here are therefore not intended to be limiting on the invention in any manner.

Every process of life is an electrochemical reaction occurring near, on, or within the cells. We now know that cell membranes are bimolecular layers of lipid molecules, with polar groups on the molecules oriented toward the inner and outer surfaces of the membrane. The membrane has a thickness of only about forty molecules and includes structures, such as channels to intake or exhaust materials for example, and also hundreds to thousands of protein macromolecules either imbedded in or extending through the membrane. The membrane can be described as a "fluid mosaic" in which many (if not all) of the macromolecules can move around the membrane over time to different locations, and the exact location and configuration of many of these macromolecule can change either as a function of, or to cause, cellular activities.

The interior of the cell is even more complex. The interior contains cytoplasmic fluid subdivided into many compartments by various types of organelles, each of which has specialized functions in cell activities. Also, the interior of the cell is criss-crossed with a complex cytoplasmic matrix of filaments and microtubules which span between the membrane and organelles, and which are believed to play a key role in controlling cellular activities.

In total, cells have an extremely complex structure and are formed from mostly nonconductive but electroactive lipid or protein molecules, each with unique electric charge distributions and thus emanating unique electric field patterns around the molecules. The electric fields of individual cell molecules combine with the electric fields of neighboring molecules, in either strength increasing or decreasing fashion, to initiate or control activities of the cell. In addition to the electric fields on or within individual cells, the cells are maintained in close relationship to adjacent cells in the three-dimensional structure of tissue, and the electric fields of all of the cells combine in either a strength-increasing or strength-decreasing fashion.

Quoting from the book *Bioelectronics*, by Stephen Bone and Bogumil Zaba (John Wiley, & Son, 1992, page 6), "We must therefore, however reluctantly admit that the prediction of the behavior of even the smallest protein, containing as it does some thousands of atoms, from a consideration of its electronic structure is a long, long way beyond our current capabilities". The complex interaction of electric fields near, on, and within cells of the body makes it difficult, and currently most often impossible, to determine what initiates what and what controls what. However it is known that natural or synthetic drugs or other chemical molecules, herein collectively described as bioactive agents, approach, align with, enter and/or react with cells based on complimentary electric charge distribution patterns of the cell and the bioactive agent molecule.

Cell membranes present a charged surface, based on the existing location and condition of the molecules on and within the cell, with the charge field extending out into the body fluids in the space between cells. Under most methods of administering bioactive agents to the body, body fluids serve to carry the agents throughout the body and to locations next to the desired cell membranes. Under the combined influence of the specific electric field pattern of the bioactive agent and the specific electric filed pattern at a receptor site, on or in the cell, most bioactive agents operate by bonding with the cell to either elicit a response from, or prevent an action of, the cell. Bioactive agents used against bacteria and viruses generally operate in the same manner.

As was noted previously, the inventor has discovered that a polarizing field, applied to the body while a desired bioactive agent is present, can modify the efficacy of the bioactive agent's reaction with cells. This modification can be an increase in the potency of the bioactive agent to such a significant degree that measurable results are obtained far above those created by the bioactive agent alone. How this effect occurs is not currently understood, but may be the result of one or a combination of the following three mechanisms:

1. The applied field may be interacting with and reinforcing or strengthening some normal charge distribution near, on, or within the cells, which results in strengthened attraction and affinity for the bioactive agent. In addition, this stronger attraction may cause more than a normal amount of the bioactive agent to accumulate in the body fluid between cells in the region of the applied field and thus be more available for reaction.
2. The applied field may be attracting or repelling the normal charge distribution near, on, or within the affected cells to an extent that rearranges the cell's receptor area charge distribution to a more favorable pattern for attracting and reacting with the bioactive agent. This may even include rotating, or moving, macromolecules of the cell, most particularity within or on the cell membrane, to new locations.
3. The applied field may be changing the normal charge distribution near, on, or within the cells in a manner which causes a normal action of the cells to occur prematurely or at an increased rate, and which increases the cell's receptivity or susceptibility to the bioactive agent. One such action could be the activation of "voltage-gated" channels, known to exist in cell membranes, which normally open and close to allow required ion passage in and out of the cells for cell metabolism, but in this case would allow increased passage of the bioactive agent to the cell's interior.

Regardless of the mechanism, the invention can be used to increase the currently known efficiency or potency of bioactive agents in relation to the treatment of various conditions and maladies. In addition, it is believed that the invention can provide beneficial use options beyond those currently available for some bioactive agents. For example:

1. Bioactive agents are administered in dose sizes known to create the desired therapeutic effect. Many bioactive agents are very expensive, and using the invention in conjunction with these agents may permit smaller doses of the agent achieve the desired effect.
2. Some bioactive agents have a therapeutic index in which the required dose size, for a desired therapeutic effect, is also close to the toxic dose size. Use of the invention with these agents may allow smaller dose sizes to achieve the desired effect with less chance of toxicity.
3. Response time to achieve the ultimate desired effect after bioactive agents are administered to the body depends on many factors, however use of the invention with the agents may decrease the response time.
4. Some bioactive agents are only marginally effective against some conditions or maladies, but provide the only currently available treatment. Use of the invention with these agents may improve the treatment outcome.
5. Some bioactive agents must be administered by routes which involve the whole body because of their particular toxic, caustic, or other properties, yet their therapeutic target may be only a small region or location of the body. Use of the invention at one or more desired regions of the body along with these agents may allow a smaller whole body dose size to be as effective as the normal larger dose, but only in the region of the therapeutic target, and thus decrease detrimental effects of the agent on the rest of the body. Alternately, the normal larger whole body dose size may be given, with the invention being used to increase the action of the bioactive agent in only a desired body region, to improve treatment there while sparing the rest of the body from the increased potency of the bioactive agent/polarizing field combination.
6. Some bioactive agents have a short effective life when administered to the body because they react with various chemicals and enzymes of the body and quickly degrade. Use of these agents according to the invention may help their desired effect to occur before they degrade.

Although there is every reason to believe the invention will be effective with many bioactive agents and diseases, the inventor's current research has centered on cancer treatment. This is a particularly important area for improvement because tumor regression and five year survival rates are unacceptably low in many types of cancer. Also, most current chemotherapy treatment regimens repetitively expose the whole body to bioactive agents just as capable of destroying many types of body cells as they are capable of destroying tumor cells. A fine line is walked in these regimens. The chemotherapy agents are given in large enough dosage, often enough, to hopefully cause tumor regression without doing more damage to the body than the cancer.

One example of use of the invention in cancer treatment would be to apply a polarizing field to increase the efficacy of the chemotherapeutic agents only in the region of the body with the tumor. This would make a standard dose regimen more potent only in the area of the cancer, thus increasing efficacy in this area while sparing the rest of the body from the increased potency. Alternately, this approach may allow the use of smaller dose regimens which spare the rest of the body from the detrimental effects of the standard larger dose regimens, but provide the efficacy of the larger regimens in the cancer location.

The inventor's research model has been the B6C3F1 mouse strain recognized by the National Cancer Institute as one Standard for chemotherapy research, and is one of the commonly accepted rodent species used in transplantable tumor studies. For the inventor's studies, female mice were implanted with murine mammary 16/C adenocarcinoma, a commonly accepted tumor for breast cancer research, and the growth rate of the tumors in Control Groups was compared to that of Test Groups which were under the influence of a polarizing field (up to 11 animals in each Group). Each study was designed to be as uniform as possible. In particular;

All test animals were approximately six weeks old, with a body weight of 17 to 20 grams at the time of implant.

Food and water were provided ad libitum throughout each study, and all Groups were exposed to the same temperature and light conditions (lights on 12 hours and off 12 hours each day).

Tumor measurements were made either by caliper, using the prolate ellipsoid formula of the National Cancer Institute, or by removing the tumor mass and weighing to 0.01 gram. The method chosen was used for all animals in each study.

Since no existing experimental protocol covers studies of this type, the inventor used altered guidelines from the National Cancer Institute's subcutaneously implanted tumor protocols #3C872 and #3CDJ2. In essence, approximately equal-sized tumor fragments were implanted in each mouse's axillary region through a puncture in the inguinal region. The tumor growth rate was then compared between groups of untreated control animals (no chemotherapeutic agent or polarizing field applied), or groups of treated control animals (treated with chemotherapeutic agent only), and groups of test animals (polarizing field and chemotherapeutic agent applied) by measuring, or removing and weighing, the resulting tumors over time. The 16/C murine mammary tumor used is particularly aggressive, and can normally grow from a barely visible, or even invisible, bump under the skin the day after the implant, to 10 to 20 percent of the animal's total body weight by day 14 (tumor size typically up to 4 grams). The tumor size for individual animals varies as the tumors grow, but the median tumor size of all groups can normally be expected to be relatively uniform if each group is set up to contain equal numbers of visible tumors of approximately equivalent size the day after the implant. After clipping the hair over the tumor site for proper inspection, the animals were divided into Groups with approximately equal tumor sizes, and a random number generator, or drawing by lot, was used to randomly assign the status of each Group as Control or Test. Extrapolating from the #3C872 Protocol, a Test Group with a median tumor weight deviating 42 percent or more from the Control Group (Test/Control, or T/C), on days 12 to 16, was considered to demonstrate abnormal (faster or slower) tumor growth. Tumor regression rates were also charted in some of the studies.

The mice in each Test Group were subjected to polarizing fields with the use of special cages or holders. The inventor has used several cage designs, depending on the goal of the particular study. All cages were constructed from polyethylene storage boxes, either 19.5 quart "Keepers" boxes from Rubbermaid Corporation, Wouster, Ohio (#2222), or 66 quart "Clear View" boxes from Sterilite Corporation, Townsend, Mass. (#1758). Other components used in the various cage types or holders will be noted in the following Study Examples, and include:

Styrene grid: a ⅜" thick plastic grid with ½" open squares (National Home Center, Plaskolite Egg Crate Light Diffuser #74507-43200).

Hardware cloth: a ¼" grid of galvanized #23 gauge wire (G. F. Wright & Wire Company, Worester, Mass., #21936-00491-7).

Acrylic sheet: either ⅛" or ¼" clear plexiglas (Cope Plastics, Little Rock, Ak.).

Screen wire: standard aluminum screen wire (local source).

Aluminum foil: Reynolds Wrap Heavy Duty (local source).

The inventor's series of studies have involved exploring the effect of a static electric field alone on cancer cell growth rates. Although a bioactive agent was not administered to the mice in this series of studies, the nutrient ions and other chemicals in the body fluids normally used by the cells served than analogousis purpose. The results were surprising, and a couple of examples are included below. Also, the results of other studies of this type are included in the inventor's copending patent application, "Intimately Worn Items for Protection from Biological Interaction with Electrostatic Fields", Ser. No. 08/488,198, the disclosure of which is included in that application is included herein by reference.

EXAMPLE A

Mice can generate significant electrostatic charges if their fur rubs over a surface. For example, after rubbing the back of mice over six inch square material samples (about a five inch rub path), the inventor measured charges on various materials of:

| Polyethylene Grid, | −2,370 volts | Glass, | −220 volts |
| Styrene Grid, | +1,970 volts | Aluminum Plate, | −100 volts |
| Acrylic Plastic, | −1,820 volts | Hardware Cloth, | −230 volts |

In each of these examples, as reflected by the law of charge conservation, equal but opposite polarity charges were generated on the surface of the animal's fur.

This effect was used in tests to generate static electric charges on mice as they moved around in cages, and the resulting tumor growth rate created by exposure to the polarizing fields of these charges was measured. In one example of this, tumor growth rates in Control Groups of mice, in minimum-charge-generating cages, were compared to tumor growth rates of Test Groups in cages with surfaces capable of generating static electric charges. After implanting the mice with tumors, the inventor set-up four groups of mice (11 animals in each group) with approximately equivalent tumor burdens in each group, in four 66 quart cages. The cages were then randomly assigned to the study methods. The Group A (control group) cage contained only a wire cage floor. The Group B cage contained a wire grid floor, and also a piece of polyester carpet suspended above the floor with the carpet fiber ends 1" above the floor, and also the carpet surface was coated with a conductive (but dry) mixture of 3% Exxon Q-14-2 cationic surfactant to quickly disperse any electrostatic charges generated. The Group C cage contained a wire grid floor plus polyester carpet (uncoated) suspended 1" above the floor. The Group D cage contained a plastic grid floor plus a piece of polyester carpet (uncoated) suspended 1" from the floor. The study design thus allowed the mice in Groups A and B to generate only low level electrostatic charges as they moved around in the cages, while Groups C and D created much higher charges as their fur rubbed against the nonconductive carpet above them. Electrostatic field measurements were made each day in each cage and typically found field levels around 200 volts in the Group A and B cages, and around 1,500 volts in the Group C and D cages.

The animals were placed in their respective cages four days after the tumor implant, and tumor size measurements were made on days 4, 7, 10, and 13. The median tumor size (in milligrams) and the ratio of each Test Group tumor to the Control Group (ratio shown in parentheses) is shown in TABLE 3:

TABLE 3

| Group | Day 4 (start) | Day 7 | Day 10 | Day 13 |
|---|---|---|---|---|
| A. | 36.5 mg | 37.0 mg | 119.8 mg | 636.0 mg |
| B. | 39.5 (8%) | 59.6 (65%) | 162.7 (35%) | 619.0 (−3%) |
| C. | 43.5 (19%) | 98.4 (165%) | 358.2 (199%) | 1,548.0 (143%) |
| D. | 41.6 (14%) | 104.6 (183%) | 362.4 (202%) | 1,459.0 (129%) |

The median tumor size of the weak electrostatic field-exposed Groups A and B remained very similar throughout the study. The median tumor size of the stronger electrostatic field-exposed Groups C and D also remained very similar throughout the study, but by day 13 the tumors in both Groups C and D were close to 2.5 times larger than the tumors in Groups A and B.

The inventor conducted a statistical analysis of the results using Fisher's Exact Tests, and Mann-Whitney U tests comparing the tumor growth in combined Groups A and B, with that of combined Groups C and D. As usual, a p-value of 0.05 or less was considered a significant difference between the Groups. None of the Groups showed a significant difference on day 4 at the start of the study. In terms of absolute tumor size, the Fisher test indicated significant group differences on days 7, 10, and 13 (p=0.034, 0.006 and 0.034 respectively). In terms of changes from day 4, the Fisher test indicated significant Group differences on days 10 and 13 (p=0.034 in each case) but not on day 7 (most likely due to the fact that Group B had a number of tumors above the overall median). With the Mann-Whitney test, absolute tumor size was significantly different on days 7, 10, and 13 (p=0.012, 0.007, and 0.010 respectively), and the changes from day 4 were also significant for all three days (p=0.023, 0.006, and 0.012 respectively). The Mann-Whitney U scores were then converted to odds of a CD animal having a larger tumor size increase than an AB on each day: day 7=2.34 to 1, Day 10=2.84 to 1, and day 13=2.86 to 1.

EXAMPLE B

To have better control over the strength and location of the electric fields used in the inventor's studies, much of his research has involved placing known electric charge levels on conductive surfaces, above and/or below the animals in the cages, to provide controlled exposure of the animals to electric fields from these charged surfaces (the animals could not contact the charged surfaces). Model #MP power supplies from Spellman High Voltage Electronics Corporation, Plainview, N.Y., were used for these studies because they provide very low output ripple, and provide a suitable static electric charge.

The inventor has conducted studies placing the Test Group mice in electric fields of various strength between charged and grounded surfaces, and compared their median tumor weight growth to Control Group mice in the same type of cage but with no electric field applied. In the following example, to explore the extreme level of accelerated tumor growth possible from exposure to a static electric field, after tumor implant a Control Group and a Test Group of mice were placed in 19.5 quart cages. Each cage had a styrene grid laid on the normal floor to keep the animals out of their wastes, and a top sheet of ⅛" thick acrylic, with electrically grounded aluminum foil covering the surface away from the animals, was animals suspended 1⅞" above the grid floor. The Control Group cage contained hardware cloth covering all plastic surfaces to minimize charge generation. An aluminum plate was placed under (outside) the Test Group cage and charged to negative 14,850 volts with a Spellman power supply to expose the Test Group mice to a strong electric field. The study was terminated on day 16, and the median tumor weight of the Test Group was 344% larger than the Control Group.

The results of the studies reported above, and those in the noted copending application, are surprising since, although possible biological effects of electromagnetic fields have received considerable attention, it has been generally assumed heretofore that a static electric field (the type of polarizing field used in the above studies) cannot exert influence in biological tissue due to the electrical conductivity of fluid in the tissue. This assumption is erroneous, as is evident from the inventor's studies; cancer cells within a mouse could not be effected by a static electric field if the field were entirely incapable of acting within the mouse's tissue. The erroneous assumption was presumably based on a principle of physics known as Gauss' law (which can be used to show that the electric field inside a perfectly conducting object is necessarily zero, unless energy is expended to maintain a voltage difference across the object). The results of the inventor's research do not disprove Gauss' law, of course, but instead make it evident that a living body cannot be viewed conceptually as a perfect conductor.

A possible theoretical explanation for the results reported above may be that a living organism is far from the homogenous conductive sphere or other shape typically used in physics classes to illustrate a zero electric field inside of a conductive object. Also, the tissue structure and dynamic, continually changing, electrochemical operation of a living organism may be far too complex to model with Maxwellian equations. A living organism is not homogeneous. For example, humans are approximately 60% water, with electrolytes to make it conductive, but 40% of the body is constructed of proteins and lipids, which rank among the best nonconductors on earth. This nonconductive 40% is the important part, and may also provide paths through which a static electric field is able to exert orientating influence into a body and effect normal metabolic activities. In any animal body, if the atoms and molecules of the nonconductive membranes of the skin cells are polarized by an external electric field, these atoms and molecules would become electric dipoles, with their normal electron distribution rearranged to create an electric field imbalance which could in turn be transmitted to adjacent cells. Each cell in the solid tissue of the body makes a number of types of intimate connections with adjacent cells, including tight junctions, desmosomes, and gap junctions. In addition, there is an extensive network of interstitial fibers, constructed of protein, connecting between cells and helping, in effect, to hold the body together. Also, there is an extensive network of nonconductive microtubules and strands spanning from the membrane through the interior of each cell. Thus, in a stepwise fashion, any electric field imbalance (possibly because of dielectric shielding inside the body) could be carried deep into the body as dipoles within these nonconductive pathways. Also, ionic polarization may occur in body fluids between the cells.

In an alternate, or possibly additional, theory of operation it may be that the continually changing natural charge distribution on, in, and around cells because of metabolic activities can be effected by an external static electric field. Although the electric field is zero inside of a homogeneous conductive object, a non-zero field can exist inside such an object if a charge is contained within a cavity in the object. The nonconductive proteins and so forth inside the body could be considered to be cavities inside of an otherwise conductive object. Also, the labyrinth of nonconductive structures in the body may create dielectric shielding which would create a nonuniform, and thus non-zero, electric field inside the body which could influence natural charge distributions on or in cells. An unnatural charge distribution on or in cells, or in the Helmholtz plane around cells, would influence their metabolic activities, and any of the previously mentioned theoretical effects could come into play at that time to favor reaction with a bioactive agent in the region.

Following the studies with electric fields alone, the inventor began studies comparing tumor growth in Control Groups of mice to that in Test Groups with a bioactive agent and a polarizing field applied. The same methods, mice, and tumor types of the previous studies were used. The measurement criteria, again extrapolated from the National Cancer Institute's test protocols #3C872 and #3CDJ2, is initial tumor size reduction. The limited treatment regimen possible with mice, and the fast growth rate of the tumor, is such that long-term regression of the tumor is not expected.

EXAMPLE C

In one study, three days after tumor implantation, the mice were separated into four Groups of equivalent tumor size, with the tumor size of each animal ranked on a scale of 1 to 5:

0.=not visible
1.=visible to under 3 mm at the longest axis
2.=3 mm to under 4.5 mm at the longest axis
3.=4.5 mm to under 6 mm at the longest axis
4.=6 mm or longer at the longest axis
5.=tumor developing the length of the implant needle track Following this the Groups were assigned to a test method using the random number generator of a calculator. The test method included assigning two of the Groups for exposure to a static electric field during days 3–6 of the test. All Groups were housed in identical 66 quart cages with a hardware cloth floor to minimize electrostatic charge generation for the duration of the test, except that the two Groups exposed to a static electric field were moved on days 3–6 to cages with a charged screen above the animals (separated from the animals with a styrene grid), a styrene grid floor, and a charge or ground plate under (outside) the cage. The distance between the top screen and outside plate was 3½" in both cages and the animals were maintained in this space without being able to touch either surface.

The treatment methods applied to the Groups were:

GROUP 1: Control Group with no bioactive agent or polarizing field applied (10 animals in the Group).

GROUP 2: Treated Control Group with 12 mg/kg adriamycin (Sigma #D4035) administered by intraperitoneal (i.p.) injection, to 11 animals, once on day 3 after the tumor implant (the tumor implant was considered day 0).

GROUP 3: Test Group with 12 mg/kg adriamycin administered i.p., to 11 animals, once on day 3, plus immediately following the injection the animals were exposed to a static electric field for 72 hours (on days 3–6) by maintaining the top screen at −5,000 volts DC, and by maintaining the outside (bottom) plate at +5,000 volts DC.

GROUP 4: Test Group with 12 mg/kg adriamycin administered i.p., to 11 animals, once on day 3, plus the animals were exposed to a static electric field for 72 hours (on days 3–6) by maintaining the top screen at −15,000 volts DC, and by grounding the outside (bottom) plate.

The treatments had time to exhibit their maximum effect by day 13, and the following TABLE 1 shows the tumor size comparisons:

TABLE 1

| GROUP 1 | GROUP 2 | GROUP 3 | GROUP 4 |
|---|---|---|---|
| Day 3 Tumor Size | | | |
| 5 | 5 | 5 | 5 |
| 4 | 4 | 5 | 5 |
| 3 | 3 | 3 | 4 |
| 3 | 3 | 3 | 4 |
| 2 | 2 | 2 | 2 |
| 2 | 2 | 2 | 2 |
| 1 | 1 | 2 | 2 |
| 1 | 1 | 1 | 1 |
| 1 | 1 | 1 | 1 |
| 0 | 0 | 1 | 1 |
| — | 0 | 0 | 0 |
| 2.2 mean | 2.0 mean | 2.3 mean | 2.4 mean |
| DAY 13 Tumor Size | | | |
| 2,583 mg | 89 mg | 385 mg | 14 mg |
| 2,527 | 44 | 48 | 14 |
| 1,762 | 31 | 33 | 0 |
| 1,313 | 28 | 12 | 0 |
| 1,162 | 6 | 12 | 0 |
| 990 | 3 | 0 | 0 |
| 882 | 0 | 0 | 0 |

TABLE 1-continued

| GROUP 1 | GROUP 2 | GROUP 3 | GROUP 4 |
|---|---|---|---|
| 685 | 0 | 0 | 0 |
| 744 | 0 | 0 | 0 |
| 149 | 0 | 0 | 0 |
| — | 0 | 0 | 0 |
| 12,797 mg (1,280 mean) | 201 mg (18.3 mean) | 490 mg (44.5 mean) | 28 mg (2.5 mean) |

In TABLE 1, the "-" in GROUP 1 indicates that this Group contained only ten mice while the remaining Groups had eleven. The results shown in Table 1 can be summarized as follows:

GROUP 1 (untreated control) illustrated the normal aggressive growth of the tumor, starting with a group tumor mean of 2.2 on day 3, then growing to a mean of 1,280 mg on day 13. Note that one animal in GROUP 1 started with a "not visible" tumor on day 3, and all mice in this group had visible tumors by day 13.

GROUP 2 (treated with adriamycin only) went from a group tumor mean of 2.0 on day 3, to 18.3 mg on day 13. This group started with 2 "not visible" tumor animals on day 3, and increased this to five not visible on day 13.

GROUP 3, treated with adriamycin plus 72 hours of a static electric field created with −5,000 volts above the animals and +5,000 volts below the animals, did worse than GROUP 2. GROUP 3 went from a tumor mean of 2.3 on day 3 to a mean of 44.5 mg on day 13. A large contribution to this mean came from one animal which had very large tumor growth (385 mg). However, dropping this animal from the Group still indicates the Group did no better than GROUP 2. This Group started with 1 "not visible" tumor on day 3, and increased this to 6 not visible on day 13. The poor showing of GROUP 3 (compared to GROUP 4) may be because the total field strength was only 10 KV compared to 15 KV in GROUP 4. However it may also be that, in this situation, charged plates on both sides of the animals did not create as favorable a condition for reactions with the bioactive agent as did a charged plate on one side and ground plate on the other. For example, the static electric field influencing Group 3 from two directions at once may be too uniform, so it could rotate but not move dipoles and charges inside the animals as much as may have occurred inside the Group 4 animals.

GROUP 4, treated with adriamycin plus 72 hours of a static electric field created with −15,000 volts above the animals and ground potential below, showed definite improvement over the adriamycin only GROUP 2. That is GROUP 4 started with a mean tumor size of 2.4 on day 3, and increased to only 2.5 mg on day 13 (7 times smaller than the adriamycin only group). Also, this group started with one not visible tumor on day 3 and increased it to 9 not visible on day 13.

In an additional indication that the electric field in GROUP 4 was increasing the adriamycin action over GROUPS 2 and 3, starting around day 25, it was noted that the animals in the three Test Groups administered adriamycin were experiencing hair loss. This is a normal reaction and is due to the fact that adriamycin destroys quickly dividing cells, such as tumor and hair follicle cells. Hair from the waste trays under each cage was collected from days 30 to 37, and it was found that GROUP 2 lost 0.16 g while GROUP 4 lost 1.95 g of hair (12.2 times more than the adriamycin only group), and that GROUP 3 lost 0.10 g (about the same as GROUP 2). Again this is a solid indication that the static electric field in GROUP 4 increased the action of the adriamycin.

EXAMPLE D

The inventor's next study confirmed that a polarizing field enhances the action of adriamycin, and also inadvertently demonstrated that a polarizing field can increase potency of a toxic bioactive agent (adriamycin) to a lethal degree. In this study, after tumor implantation, the mice were separated into four Groups of equivalent tumor size and placed in hardware cloth floored cages. There were eleven mice in each Group. The Groups were randomly assigned as:

GROUP 1: Treated Control with an i.p. injection of 8 mg/kg adriamycin on days 3 and 5. No exposure to polarizing fields.

GROUP 2: Test Group with an i.p. injection of 8 mg/kg adriamycin on days 3 and 5. Immediately following each injection, the animals were moved into a cage where they were exposed for four hours to a static electric field between a top sheet of aluminum foil (sealed between two 1/8" thick plexiglas sheets) 1¼" above the animals and a grounded aluminum plate under (outside) the cage. A potential of −15,000 volts DC was applied to the aluminum foil. The distance between the top aluminum foil and the outside grounded plate was 3⅝" and the animals were maintained between the top foil and outside plate on a styrene grid floor. The animals were moved back into hardware cloth floored cages after the four hour exposure.

GROUP 3: Test Group with an i.p. injection of 8 mg/kg adriamycin on days 3 and 5. Immediately following each injection, the animals were moved to a cage (like that of GROUP 2) for a four hour exposure to continuing cycles of 15 minutes of −15,000 volts DC applied to the aluminum foil above them and 15 minutes of +15,000 volts applied to the aluminum foil. The animals were moved back into hardware cloth floored cages after the four hour exposure.

GROUP 4: Test Group with an i.p. injection of 8 mg/kg adriamycin on days 3 and 5. Immediately following each injection, the north seeking pole of a ½" diameter by 3/16" thick 10,800 gauss rare earth magnet (8 lb. holding force) was glued to each animal over the tumor site with 2 small drops of #6001 Super Glue Gel (3M Company). Following this, for the next four hours, each animal was restrained in a clear 1¼" OD by 1⅛" ID by 4¾" long plexiglas tube to prevent the animals from removing the magnets. The plexiglas tubes were placed far enough apart to prevent intermingling of the magnetic fields, and after four hours the magnets were removed and the animals placed back in a hardware cloth floored cage.

By day 10 (5 days after the second injection), while the tumors were relatively small in all Groups, animals in the three Test Groups started dying, indicating that the polarizing fields (static electric fields in the case of GROUPS 2 and 3 and static magnetic fields in the case of GROUP 4) had increased the potency of the normal adriamycin effect to a level beyond tolerance by the bodies of the mice. Also, the animals with the smallest tumors died first, indicating enhanced adriamycin action on both the tumors and the bodies of these animals. The following TABLE 2 shows the mortality dates of animals in the Test Groups, compared to the Control Group, over the 30 day study.

TABLE 2

Mortality Days

| Day | GROUP 1 | GROUP 2 | GROUP 3 | GROUP 4 |
|---|---|---|---|---|
| 0. | | Implant Tumors In All Groups | | |
| 1. | | | | |
| 2. | | | | |
| 3. | | First Injection All Groups | | |
| 4. | | | | |
| 5. | | Second Injection All Groups | | |
| 6. | | | | |
| 7. | | | | |
| 8. | | | | |
| 9. | | | | |
| 10. | | | | XXX |
| 11. | | | X | X |
| 12. | | XXX | XXXXXX | XX |
| 13. | | | | X |
| 14. | | | | |
| 15. | | | | |
| 16. | | | | |
| 17. | | | | |
| 18. | | X | | |
| 19. | | X | | |
| 20. | | | | |
| 21. | | | | |
| 22. | | X | | XX |
| 23. | | | | |
| 24. | | | | |
| 25. | | | | X |
| 26. | | | | |
| 27. | | | | X |
| 28. | | X | | |
| 29. | | | | |
| 30. | X | | | |

The results shown in TABLE 2 can be summarized as follows;

GROUP 1 (treated with adriamycin only) had one animal die at day 30, and this was from the effect of the tumor, not the adriamycin. By this time the tumors had developed to an average weight in this group of 12% of the animals' total body weight.

GROUP 2 (adriamycin plus a static electric field due to −15,000 volts DC on the top foil) lost half of it's animals by day 22 and all of these deaths could be attributed to the increased potency of the adriamycin since the average tumor weight in the group was only about 2% of the average body weight at this time. Only four live animals remained in this group at day 30, and their average tumor weight was 1,189 mg compared to 2,357 mg for Control Group 1.

GROUP 3 (adriamycin plus 15 minute cycles of 15 minute negative then positive 15,000 volt DC fields) lost half of it's animals by day 12 and all of these deaths could be attributed to the increased potency of the adriamycin since the average tumor weight in the group was less than 2% of the average body weight at this time. Only four live animals remained in this group at day 30, and their average tumor weight was 1,400 mg compared to 2,357 mg for Control Group 1.

GROUP 4 (adriamycin plus a static magnetic field) lost half of it's animals by day 12 and all of these deaths could be attributed to the increased potency of the adriamycin since the average tumor weight in this group was only about 0.6% of the average body weight at this time. All of the animals in this group had died by day 30.

Examinations of the first 50% of animals to die in each Test Group showed kidney and possible liver damage. This would be expected because adriamycin is known to normally concentrate in both. Also, there appeared to be heart enlargement in many of the Test Group animals, and irreversible myocardial toxicity with delayed congestive heart failure is a sign of adriamycin overdose. Like all drugs, particularly chemotherapeutic agents, adriamycin will kill the body above a certain dose potency level. In this study, the same dose level was given to all animals, and was tolerated by the treated control group. But the various polarizing fields the Test Groups were exposed to increased the potency of the dose to a lethal level, even though the fields were only applied for four hours after administering the chemotherapeutic agent.

Observing the same effect from both static electric and static magnetic fields supports the conclusion that both types of field influence normal orientation and distribution of, and possibly movement of, charges and proteins in the body. It also supports the conclusion that both types of field accelerate cancer growth (most likely by influencing the normal orientation and distribution of, and possibly movement of, charges and proteins in the body) and that the cancer cells consequently, either ingest more adriamycin than they otherwise would or become more susceptible to adriamycin poisoning.

In this study the static magnetic fields appeared to have a stronger effect than the static electric fields. Magnetic fields are known to penetrate tissue almost unimpeded, and this may account for the study findings. However, in this study, the magnetic force field would also have been much stronger than the static electric field applied, both because the magnets were very strong, and because the magnets were very close to each animal whereas the aluminum foil connected to the power supply was over 1" away. Also, without a second plate for the magnetic fields to connect with, the magnetic fields would have been even more nonuniform than that of the electric fields.

The inventor believes the applied static magnetic fields in this Study would operate in a different manner than the static electric fields, but the ultimate results may be the same. Static magnetic fields easily penetrate tissue, but they do not influence electric charges unless the charges move in relation to the magnetic field (or unless the field moves in relation to the charges). The metabolism of the body constantly moves, separates, or combines electric charges (polar molecules) in and around the countless proteins and lipids we are made of. The applied magnetic field may have oriented and influenced these naturally moving charges to move in an unnatural direction. This would have caused a separation and aggregation of these charges over time. Each of these charges has a static electric field of its own, and the combined static electric field influence of this unnatural grouping of charges at the cellular level could result in any of the above noted actions being possible because of externally applied static electric fields.

Also in this study, the polarizing fields were affecting all of each animal's body, and thus increasing the action of the adriamycin in all parts of the body. This is true for even the magnetic fields; the magnets were placed in one location but their force field lines connected from the north pole to the south pole and this path would engulf the entire animal, which was only about 2½" long. In human patients, it would be possible, and most often desirable, to confine the polarizing field effect to only a select body region for maximum therapeutic effect in that region while sparing the rest of the body from the increased effect.

EXAMPLE E

In the inventor's next study, after tumor implant, the mice were separated into four groups of equivalent tumor size and randomly assigned as:

Group 1: (10 animals) Treated Control with i.p. injection of 12 mg/kg adriamycin on day 4. No exposure to polarizing fields.

Group 2: (11 animals) Test Group with an i.p. injection of 12 mg/kg adriamycin on day 4, then 10 days exposure to a 15,000 volt static electric field in a cage with a plastic grid floor, a charged top plate of screen wire sealed between two ⅛" thick sheets of plexiglas, and a grounded wire grid under the cage 3½" from the charged top plate (animals could not touch the ground or charged screen). The charge on the top plate screen wire was continuously cycled each 15 minutes between positive 15,000 volts and negative 15,000 volts.

Group 3: (11 animals) Test Group with an i.p. injection of 12 mg/kg adriamycin on day 4, then 10 days exposure to a 15,000 volt static electric field in a cage with a grounded wire grid floor and a charged top plate of screen wire sealed between two ⅛" thick sheets of plexiglas 4½" from the floor (approximately 3½" from the animal's back to the charged screen). The animals were touching the grounded floor, but could not touch the charged screen. The charge was continuously cycled each 15 minutes between positive and negative 15,000 volts.

Group 4: (11 animals) Test Group with an i.p. injection of 12 mg/kg adriamycin on day 4, then 10 days exposure to a 15,000 volt static electric field in a cage with a plastic grid floor, a charged top plate of screen wire sealed between two ⅛" thick plexiglas sheets, and no nearby ground surface (the nearest ground was a concrete floor 4'3" away). The charge was continuously cycled each 15 minutes between positive and negative 15,000 volts.

At three different times during the study, a Leeds and Northrup 0.1 sensitivity microampere meter was used to measure any current flow to ground in the Group 2 and 3 cages (only groups with a nearby ground). No current flow was detected for either Group.

Tumor weight was measured and averaged for each Group starting at the time of injection and field exposure (Day 4), then on days 8, 11, and 14. Table 4 shows the percentage of tumor weigh loss (regression) or gain for each Group from day 4:

TABLE 4

|  | DAY 8 | Day 11 | Day 14 |
|---|---|---|---|
| Group 1: | −26% | −3% | +110% |
| Group 2: | −79% | −81% | −86% |
| Group 3: | −68% | −78% | −64% |
| Group 4: | −72% | −75% | −51% |

The three static electric field exposed Groups did considerably better than the adriamycin only Group, with the mean tumor weight of the field exposed Groups more than three times smaller than the adriamycin only Group by day 14. A Statistical analysis of the results, using both non-parametric and parametric methods, was also conducted for each measurement day. There was no statistically significant difference in the tumor sizes of any of the Groups on day 4. The three field exposed Groups demonstrated significant tumor regression over the adriamycin only Group on all three days, with probability values as low as 0.001. Also, the odds that an animal treated with field exposure would do better than an adriamycin only treated animal were as high as 8.3 to 1.

EXAMPLE F

In the inventor's next study, tumor bearing mice in four groups were first injected with 10 mg/kg adriamycin then each group was alternately placed in wire grid floor cages for rest, and 1¼" OD×⅞" ID×3½" long clear polycarbonate restraining tubes for exposure to polarizing fields (the animals in the Treated Control Group 1 were placed in the same type of tubes, but polarizing fields were not applied). The restraining tubes for all animals were placed on special holders during each field exposure period, with a polarizing field element placed next to each tumor (on the outside of the tube) for the Group 2, 3, and 4 animals (no field element was used for the Group 1 animals). All restraining tubes were placed far enough apart to minimize interaction of the various polarizing fields used during each exposure period. The schedule for all groups in and out of the cages and restraining tubes was:

4 hours in restraining tubes,
9 hours in cages,
8 hours in restraining tubes,
8 hours in cages,
8 hours in restraining tubes,
12 hours in cages,
8 hours in restraining tubes,
7 hours in cages,
8 hours in restraining tubes,
the remainder of the 20 day study in cages.

Seven days after tumor implant, the inventor separated the mice into four groups of equivalent tumor size and randomly assigned the groups as:

Group 1: (10 animals) Treated Control with an i.p. injection of 10 mg/kg adriamycin on day seven. No exposure to polarizing fields.

Group 2: (11 animals) Test group with an i.p. injection of 10 mg/kg adriamycin on day seven, then exposure to a cycling 15,000 volt static electric field emanating from a ¼" brass ball maintained next to each animal's tumor (ball outside of the restraining tube). Each brass ball in this group was connected to a DC power supply in which the output changed from positive 15,000 volts to negative 15,000 volts each 5 seconds throughout each field exposure period.

Group 3: (11 animals) Test group with an i.p. injection of 10 mg/kg adriamycin on day seven, then exposure to a constant 15,000 volt static electric field emanating from a ¼" brass ball maintained next to each animal's tumor (ball outside the restraining tube). Each brass ball in this group was connected to a negative 15,000 volt DC power supply throughout each field exposure period.

Group 4: (12 animals) Test group with an i.p. injection of 10 mg/kg adriamycin on day seven, then exposure to the north-seeking pole of a 10,800 gauss static magnetic field emanating from ½" diameter by 3/16" thick rare earth magnet maintained next to each animal's tumor (magnet outside the restraining tube) throughout each field exposure period.

Tumor weight was measured and averaged for each Group starting at the time of injection and field exposure (day 7), then on days 11, 14, 17, and 20.

TABLE 5 shows the percentage of each Group's mean tumor weight loss (regression) or gain from day 7, with the numbers in parentheses showing the Group median tumor weight loss or gain percentage from day 7.

TABLE 5

|  | G1 | G2 | G3 | G4 |
|---|---|---|---|---|
| Day 11 | +14% (+29) | −46% (−18) | −53% (−42) | −70% (−71) |
| Day 14 | +24 (+33) | −40 (−36) | −58 (−55) | −70 (−76) |

TABLE 5-continued

|  | G1 | G2 | G3 | G4 |
|---|---|---|---|---|
| Day 17 | +225 (+75) | +59 (+77) | +35 (+25) | −34 (−42) |
| Day 20 | +1,110 (+910) | +807 (+940) | +596 (+547) | +272 (+64) |

Again, as with the previous studies, the polarizing field-exposed Groups did remarkably better than the adriamycin only Group.

Group 1, the adriamycin only group did not achieve mean or median tumor size reduction at any measured point in the study. The inventor believes the normal tumor growth rate was simply slowed by the adriamycin.

Group 2, exposed to 5 second cycles of positive then negative 15,000 volts, achieved statistically significant tumor regression through day 14, but not as much as Group 3. The inventor's previous studies have shown 15 minute cycles of positive then negative cycles 15,000 volts creating more enhancement of the adriamycin than a constant (same polarity) charge. The 5 second cycle time in this study then appears to be approaching the lower (shorter) cycle time for efficacy, and the inventor feels changing the polarity or strength of the polarizing fields in times less than 1 second would have very little efficacy.

Group 3, exposed to a constant negative 15,000 volt field, achieved statistically significant tumor regression through day 17. Thus this group demonstrated the strongest adriamycin enhancement of the two electric field exposed groups.

Group 4, exposed to a 10,800 gauss static magnetic field, achieved statistically significant tumor regression lasting throughout the 20 day study. The inventor's previous studies have shown that this magnetic field can provide adriamycin enhancement at a higher level than a 15,000 volt static electric field.

A statistical analysis of the probable significance of the differences in tumor weight loss/gain of the polarizing field exposed groups, compared to the adriamycin-only Group 1, was conducted using a Kruskal-Wallis analysis of variance followed by Mann-Whitney tests of the pairwise differences between Groups 2, 3, and 4 with Group 1. Also, the resulting U statistic was transformed into the odds that an animal treated in the manner of 2, or 3, or 4, would have more of a decrease (or less of an increase) in tumor weight than an animal treated with adriamycin only. TABLE 6 shows the probability values for each day, with the odds shown in parentheses (4 to 1 odds that an animal in Group 2 would do better than an animal in Group 1 is the first figure for example). There was no statistically significant difference in the tumor sizes of any of the Groups on day 7 (p=0.181).

TABLE 6

|  | Group 2 | Group 3 | Group 4 |
|---|---|---|---|
| Day 11 | p = 0.0166 (4) | p = 0.0038 (7) | p = 0.0001 (39) |
| Day 14 | 0.0038 (9) | 0.0015 (10) | 0.0001 (119) |
| Day 17 | 0.0783 (3) | 0.0091 (5) | 0.0015 (9) |
| Day 20 | 0.7247 (1) | 0.1809 (2) | 0.0295 (3) |

Adriamycin is known to degrade quickly in the body environment, with cleavage of the glycosidic group and changes in the 4-hydroxy group breaking the material down into less effective metabolites which are quite different than adriamycin. The alpha phase half-life is approximately 1 hour, and the beta phase half-life can run 21 to 48 hours. Beyond this, a detectable level of the metabolites may persist in the serum for over a week. Without question, both the static electric and static magnetic fields successfully enhanced the action of both adriamycin and its metabolites against the tumors.

In total, the inventor's studies demonstrate that static electric and static magnetic fields can increase the potency and efficacy of bioactive agents on the body. The fact that these fields exhibit an influence on tumors without a chemotherapeutic agent applied, and also exhibit influence on cells other than tumors, such as hair, kidney, liver, and heart cells, indicates that the invention will be useful with other types of bioactive agents and diseases. For treatment purposes, the power, application method, and time of application of the polarizing electric and/or magnetic fields in a specific treatment will depend upon factors such as, for example, the bioactive agent used, the type and location of the malady or disease, and the treatment goal. In most cases a preferred bioactive agent for treatment of a specific disease will be known, and the desirability of the bioactive agent/polarizing field combination can be determined with standard protocols and animal models of the disease, typically using an escalating dose level, such as a modified Fibonacci series, for example.

The benefits from the invention could be tremendous. For many maladies, a few percent increase in efficacy of the bioactive agent used can make the difference in whether treatment is successful or not. Consider the following highly simplified example with cancer:

Depending on the tumor type and it's location, cancer cells can divide (or double) in time frames ranging from less than 24 hours to numbers of days. Assume a cancer patient has 100 cancer cells which normally double each 7 days. Typically, a patient's body cannot withstand powerful chemotherapy treatments on more than a monthly basis. If, during week one, the patient undergoes a chemotherapy treatment which kills 85% of the cancer cells, 15 viable cells would remain (day 7). During week two the 15 cells would double into 30, then week three 60, then week four 120. By the start of week five, and time for the second chemotherapy treatment, the patient would have 20 more cancer cells than before the first treatment, and would be losing the battle against exponential cell growth.

Consider the outcome of this example if the invention were used to increase the effectiveness of the treatment by just 6%, killing 90 cancer cells instead of 85. Again, the patient would start with 100 cancer cells. The first chemotherapy treatment would reduce this to 10 on day seven, and they would then double to 20 cells at week two, 40 cells at week three, and 80 cells at week four. By the start of week five and time for the second chemotherapy treatment, the patient would have 20 fewer cancer cells and would be winning the battle.

It is anticipated that the invention can be used in any method in which increasing the action of a bioactive agent would be desirable. The optimum treatment will in most cases depend on a number of factors such as the bioactive agent, the response desired, and the body location targeted for treatment, for example. Examples of treatment methods in accordance with the invention, for both static electric and static magnetic fields, include:

1. Exposing all, or some select portion, of the body to a nonuniform, or to a relatively uniform, polarizing field during a period while a desired bioactive agent is present in or on the body.

2. Exposing all, or some select portion, of the body to a nonuniform, or a relatively uniform, polarizing field during a period while a desired bioactive agent is present in or on the body, in a manner where the polarizing force of the field is of one polarity for a period of time of at least one or more seconds, then changing the polarity for another period of time of at least one or more seconds. Cycling the polarity in this manner will be done in periods long enough to allow increased efficacy of the bioactive agent to occur, yet in periods short enough to avoid Coulomb blockade, in which charges accumulate, over time, under the influence of the field in great enough numbers to block part of the effect of the field. Also, occasionally changing the polarity can be used to maximize the possibility of creating a cellular condition which favors reaction with the applied bioactive agent. For example, it is anticipated that a static electric field may be able to rotate and/or move molecules, in or on the cell membrane. Such movement would occur very slowly, and specific locations of the molecule along the movement path may favor reaction with the applied bioactive agent due to the combined effect of the charge distribution on the molecule and on neighboring sites the moving molecule passes by. The moving molecule would eventually reach a point where it could no longer move in response to the polarizing field, and this would reduce some of the extra chance of creating a condition favoring reaction with the bioactive agent. Reversing the field polarity (or changing the location of the field emanating source) would then place the molecule under the influence of a force with a different vector direction, again moving the molecule and maximizing opportunities to create conditions favoring reaction with the bioactive agent.

3. Exposing all, or some select portion, of the body to a nonuniform, or a relatively uniform, polarizing field during a period while a desired bioactive agent is present in or on the body, in a manner where the strength (amplitude) of the field is increased and/or decreased over time. Increasing and/or decreasing the strength of the field in this manner would allow different degrees of cellular actions to occur at each field strength level and thus insure that reaction with the bioactive agent will occur even if only one specific level of field strength favors the reaction.

4. Exposing all, or some select portion of, the body to a nonuniform, or a relatively uniform, polarizing field during a period while a bioactive agent is present in or on the body, in a manner where the field approaches the body from one or more directions for a period of time, then changes to one or more additional or different directions for another period of time. The periods of time may be equal or different. This method helps avoid Coulomb blockade, and also exposes the target tissue region, and ultimately each cell, to a polarizing force from different directions to ensure that cellular reaction with the bioactive agent will occur even if only one of the directions favors the reaction. This method may also move molecules or charges along a travel path which maximizes opportunities (as noted in #2 above) to create conditions favoring reaction with the bioactive agent.

5. Any combinations of the above methods may be used to meet specific needs.

The attached drawings show a few examples of basic embodiments and methods of use to aid in understanding the invention.

FIG. 1 shows a preferred embodiment for exposing all, or a large portion, of a patient's body to the influence of a polarizing field (here a static electric field). The patient 1 is placed on a treatment element, shown in this example as treatment pad 2, which contains a conductive element (not shown in FIG. 1) covered and insulated from contact with the patient's body. A terminal 3 is connected to the conductive element in the treatment pad 2, and the patient is exposed to a nonuniform static electric field during the period that a power supply (not shown in FIG. 1) is applied to the conductive element via the terminal 3 so as to maintain a charge on the conductive element. The field strength and/or polarity may be periodically changed during the treatment if desired.

If desired for a particular treatment method, an additional conductive element 4 may be positioned above the patient. A terminal 5 is provided to permit the conductive element 4 to be connected to ground, or to a power supply. Grounding conductive element 4 will provide a relatively uniform static electric field between treatment pad 2 and conductive element 4 to which the patient is exposed. Supplying conductive element 4 with a voltage having a different polarity from that supplied to treatment pad 2 will also provide a relatively uniform static electric field between treatment pad 2 and conductive element 4. Supplying conductive element 4 with a voltage having the same polarity as that supplied to treatment pad 2 will provide a nonuniform polarizing force field between treatment pad 2 and conductive element 4.

In an example of an alternate use, to meet specific needs, conductive element 4 may be periodically charged alone by the power supply, or charged while the conductive element in treatment pad 2 is grounded, to have the static electric field approach the patient from a different direction than treatment pad 2.

In still another alternate use example, the field strength and/or polarity emanating from treatment pad 2 and/or conductive element 4 may be periodically changed during the treatment if desired.

Also, treatment element 2 may contain more than one conductive element, with the conductive elements insulated one from another, and a static electric charge may be alternately applied to the different conductive elements to have the polarizing field approach the patient from different locations. In this same regard, different strengths or polarities of charge may be applied to the different conductive elements to control the power and direction of the polarizing field reaching the patient's body.

As an alternative to laying the patient directly on treatment pad 2, the patient may be laid on a nonconductive surface, and the charged conductive element may be placed at some other location under (or even above) the patient. This method would also accommodate placing the charged conductive element at an angle to, instead of parallel with, the patient's body to expose the patient to a nonuniform static electric field which also has different gradients which may enhance movement of molecules and charges within the patients body to achieve a charge distribution favoring reaction with the bioactive agent. Other placements of treatment pad 2 and conductive element 4 may also be used to create field gradients, such as placing treatment pad 2 parallel to the patient and conductive element 4 at an angle to treatment pad 2 for example.

Also, it will sometimes be desirable that treatment pad 2 and conductive element 4 be of different size. For example, if conductive element 4 is smaller than treatment pad 2, more nonuniform fields are created between treatment pad 2 and conductive element 4 around the edges of conductive element 4, and conductive element 4 can be positioned to have these more nonuniform fields interact with the target regions of the patient's body.

Figure 2:
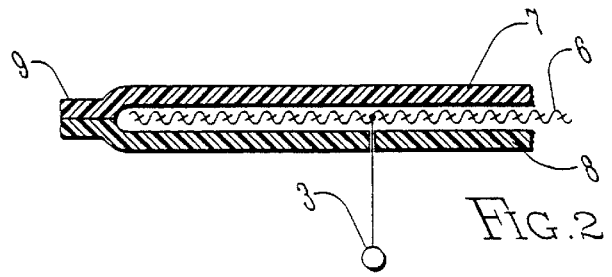
FIG. 2 is a cross-sectional view illustrating a portion a treatment element shown in FIG. 1.

FIG. 2 is a cutaway portion of an example of a suitable structure for a treatment element such as treatment pad 2 in FIG. 1. The previously-mentioned conductive element is identified by reference number 6 in FIG. 2 and is sandwiched between two insulating covers 7 and 8. The conductive element 6 may be any electrically conductive substance, however flexible substances such as silver coated fabric (Monsanto Metallized Materials, St. Louis, Mo. for example) or wire cloth (Tetko, Inc., Briarcliff Manor, N.Y. for example) are preferred. The insulating covers 7 and 8 may be any electrically insulating substance, however puncture resistant flexible substances, such as nylon laminates for example, which can be heat sealed at 9 around the edges to encase the conductive element 6, are preferred. Allied Corporation, Morristown, N.J. and Printpack, Inc. Grand Prairie, Tex. are examples of suppliers of such nylon materials. The insulating cover must be thick enough to prevent the electrical charge chosen for the conductive element 6 from arcing through the insulating cover if the patient inadvertently touches a ground, or opposite potential, while the conductive element 6 is charged. For example, Allied's nylon-6 film has a dielectric strength of about 700 volts/mil, and a safety factor must be included. A 1000% safety factor, for example, would reduce this to 70 volts/mil, and if the conductive element 6 is intended to carry 5,000 volts, the insulating cover 7 over the conductive element 6 would need to be at least 0.071" thick. Fabrics or other surfaces such as blankets, etc., may be placed on top of the insulating cover 7 for patient comfort, and also the treatment pad will conform to the patient's body if it is placed on top of an insulated mattress, etc.

The additional conductive element 4 of FIG. 1 may be constructed in the same manner as shown in FIG. 2, and this additional conductive element may be laid directly on top of the patient. However, more control over the static electric field is achieved (as the patient moves around, etc.) by suspending the conductive element 4 above the patient from an insulated stand. In this situation it is preferable that conductive element 4 be rigid, and a convenient way to accomplish this is to use rigid material, such as acrylic sheet (Rohm & Haas Company, Philadelphia, Pa.) for example, as the insulating covers 7 and 8, and to seal around the edges at 9 with RTV silicone or other materials to encase the conductive element. Acrylic has a dielectric strength around 350 volts/mil, and again the required thickness of insulating covers 7 and 8 would depend on the maximum voltage they are expected to be subjected to.

Figure 3:
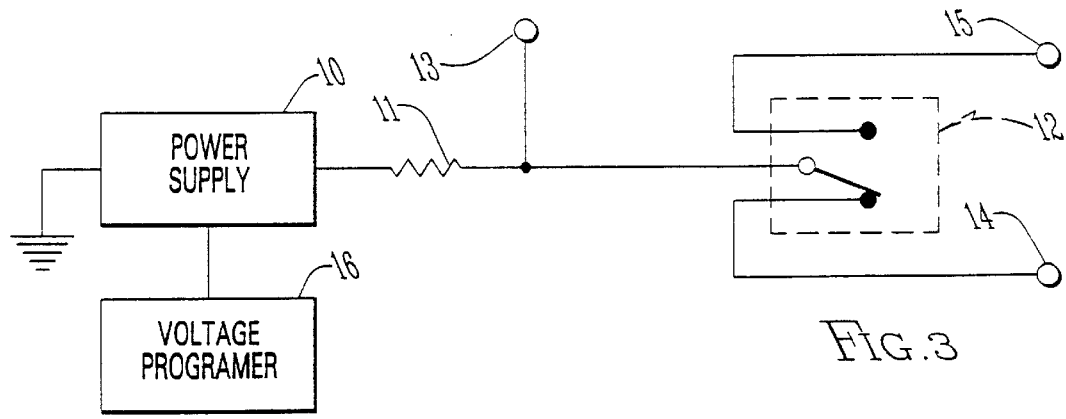
FIG. 3 is a block diagram of an embodiment of a power supply system which can be used with the arrangement shown in FIG. 1.

FIG. 3 shows an example of a power supply system used for placing charge on the conductive element 6 in FIG. 2 from an output 13. The power supply 10 for charging the element 6 may be as simple as an electrostatic charge generator, such as a Wimshurst or Van de Graaff generator for example. Or alternately, the treatment element may comprise a self-contained electret. However, well controlled and regulated high-voltage DC power supplies are widely available and generally preferred because the voltage is easily maintained and controlled. Spellman High Voltage, Plainview, N.Y. and American High Voltage, Alpine, Calif. are examples of suppliers offering high voltage DC power supplies with adjustable outputs ranging from 100 to as much as 100,000 volts in either negative or positive potential, or both. These supplies may be specified with current limiting circuits which shut down the supply if a specific current level is exceeded, and thus minimize danger to the patient in case of a short circuit, etc. Maintaining the static electric field requires almost no current flow, only enough to bring element 6 to a desired charge level and then maintain that level. A current limiting resister 11, such as a high-voltage resistor from Cesiwid, Inc., Niagara Falls, N.Y. for example, typically with a resistance around 1 megohm to 20 megohms depending on the power supply voltage, is preferably placed in the circuit as an additional safety measure for the patient. A single pole-double throw high-voltage relay 12, available from Kilovac Corp., Santa Barbara, Calif. for example, or other switching technique, is optional and shown as a convenient method of changing the charge from one location to another, such as from treatment pad 2 below the patient to the additional conductive element 4 above the patient, for example. For this purpose, a relay terminal 14 is connected to the terminal 3 of the treatment pad 2 and a relay terminal 15 is connected to the terminal 5 of the conductive element 4. A timer (timer and relay coil not shown) periodically energizes the relay coil to control the time that the charge is maintained at each location. This would expose the patient to a nonuniform static electric field alternately approaching the body from different directions to ensure that cellular reactions occur with the bioactive agent even if the reaction favors only one direction at a certain point in time. This would also minimize Coulomb blockade, and dielectric shielding.

As an additional option, an output voltage programmer 16, such as a Digital to Analog converter and a suitably programmed computer (Datel, Inc. Mansfield, Mass., for example) may be used to slowly increase or decrease the voltage of any of the outputs (by driving the standard remote voltage control circuit of the supply) to ensure that the desired cellular reaction with the bioactive agent occurs even if only one range of voltage levels favors the reaction at a certain point in time.

FIG. 4 shows a power supply system which utilizes a double pole-double throw relay 17 as a convenient way of periodically changing a ground and a charge potential between two locations, such as between the treatment pad 2 below the patient and the additional conductive element 4 above the patient for example, by way of terminals 18 and 19. This would expose the patient to a relatively more uniform static electric field with its field alternately approaching the patient in different directions to ensure that cellular reactions with the bioactive agent occur even if only one direction favors the reaction at a certain point in time. This would also minimize Coulomb blockade. A timer (timer and relay coil not shown) periodically energizes the relay 17 to control the desired time of the field from one direction.

In an additional use of the power supply system of FIG. 4, the lower contact of relay 17 may be disconnected from terminal 19. In this configuration, when relay 17 is not activated, the voltage from the power supply 10 would be applied to terminal 18 but ground would not be applied to terminal 19. When relay 17 is activated, the voltage would be applied to terminal 19 and ground would be applied to terminal 18. If, for example, terminal 18 is connected to the terminal 5 of the additional conductive element 4 above the patient and terminal 19 is connected to the terminal 3 of the treatment pad 2 below the patient, this relay configuration would allow a nonuniform polarizing force field to be applied to the patient while the coil of relay 17 is not activated, and then a relatively more uniform field to be applied while the coil of relay 17 is activated. This situation would first allow the nonuniform field to maximize bioactive agent reactions possible with that type of field for some period, then a periodic change to a relatively more uniform field would allow bioactive agent reactions favoring that type of field to occur for some period.

FIG. 5 shows an example of a further power supply system using power supplies 20 and 21 of different polarity to provide positive and negative voltages to two different locations from terminals 22 and 23. An example of this use would be applying a negative potential from terminal 22 to the additional conductive element 4 in FIG. 1, and a positive potential from terminal 23 to the treatment pad 2 in FIG. 1, to expose the patient to a strong, relatively uniform, static electric field without requiring an excessively high voltage on either the treatment pad 2 or the conductive element 4. In an optional use, a double pole-double throw relay 24 having terminals 25 and 26 may be used to periodically change the charge polarity between two locations, such as treatment pad 2 and conductive element 4 in FIG. 1 for example, to minimize Coulomb blockade and also ensure that cellular reactions with the bioactive agent will occur even if only one of the polarity locations favors the reactions at some point in time.

Also, in another use of the power supply system of FIG. 5, only one treatment pad, such as treatment pad 2 in FIG. 1 for example, may be connected to either terminal 25 or 26 of relay 24, and the polarity of the voltage applied to the treatment pad will be reversed each time relay 24 switches position. A timer periodically energizes the relay coil (timer and relay coil not shown) to control the desired time both polarities are maintained at their respective locations. This exposes the patient to a nonuniform field from one location, but with the polarity reversed each time relay 24 is switched. This maximizes opportunities for creating conditions favoring reaction with the bioactive agent even if the reaction favors only one polarity at different points in time. Also, this minimizes any effects of Coulomb blockade. The additional conductive element 4 may be provided and grounded if a relatively uniform force is desired for a specific treatment.

Figure 4:
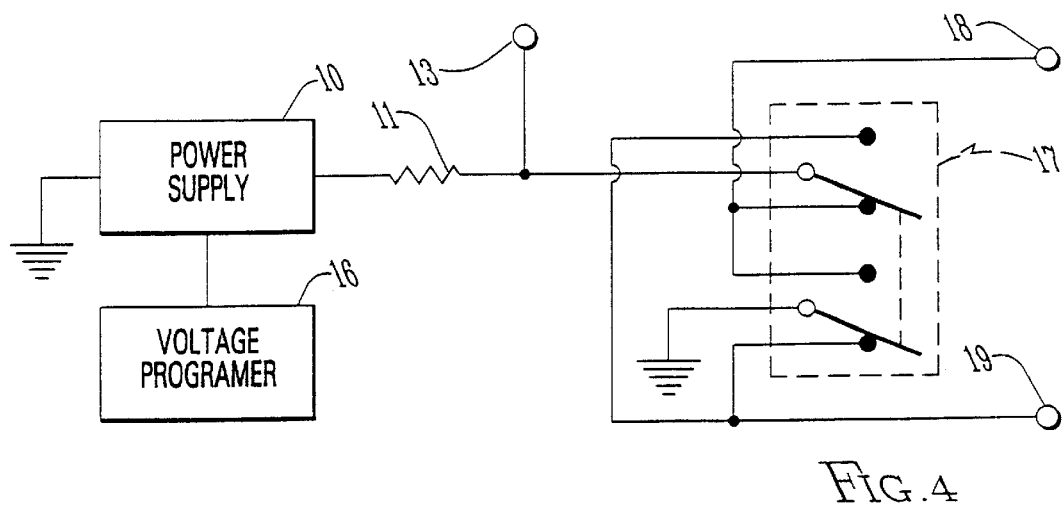
FIG. 4 is a block diagram of another embodiment of a power supply system.

It is noted that solid state switching may be used in place of the relays of FIGS. 3–5 if the required treatment voltage is low enough to be handled by semiconductors. In addition, multiple power supplies may be used, instead of the high-voltage relays of FIGS. 3–5, to apply desired voltages to treatment pads at various locations, with the timing of the voltage application to each location being controlled by switching the power supplies on and off. Also, other output and timing options are possible to provide optimum action of the invention with specific bioactive agents or treatment needs.

FIG. 6 shows a preferred embodiment of a method of applying an electric field to only a target region of the body. This would most often be a preferred use of the invention, and would increase the potency of the administered bioactive agent in only the target region while sparing the rest of the body from the effect of the increased potency. A treatment element, shown here as treatment pad 27, is positioned on (adhered to, etc.) a body target region. Treatment pad 27 contains a conductive element which is encased in insulating material, and has a terminal 28 so a desired electric charge may be applied to the conductive element. A properly sized version of the treatment pad construction shown in FIG. 2 would serve well as treatment pad 27. Terminal 28 to the conductive element may be connected to any output of the power supply systems shown in FIGS. 3–5, or to other desired power systems, to apply the desired type of nonuniform polarizing force field to the body target region. As an option, an additional treatment pad 29, containing an insulated conductive element and a terminal 30 connected to the conductive element, may be applied to the body region, and be grounded, or receive output from any of the power systems shown in FIGS. 3–5, or other desired power systems. Such an option may be used to provide a relatively uniform, or nonuniform, static electric field between treatment pads 27 and 29, and/or help direct the action of the static electric field through specific tissue areas.

It is noted that power supply systems for use with the invention may be constructed small enough to comfortably wear on a belt, etc., and the insulated treatment elements, may be maintained in place on the patient for long-term treatment as the patient moves about.

FIG. 7 shows a preferred embodiment of a method of applying the invention to an internal target body region (in this case the stomach) by inserting a fully insulated conductive element 31 into any body cavity so as to bring it as close as possible to the target region for maximum effect, and also to aid in confining the effect to only the target region. Conductive element 31 may be of any desired shape to aid insertion into the body cavity, and also to help expose the target region to the static electric field. Terminal 32 may be connected to element 31 by shielded cable to isolate the field from undesired body areas. Terminal 32 may be connected to any desired power system to apply the desired type of static electric field to the body target region. As an option, one or more treatment pads 33, containing an insulated conductive element connected to a terminal 34, may be applied externally. The treatment pad or pads 33 may be grounded, or receive input from a power supply system, to provide a relatively uniform, or nonuniform, static electric field between the conductive element 31 and the treatment pad or pads 33, and/or help direct the action of the static electric field through specific tissue regions. In some cases, it may be desirable to surgically implant the conductive element 31 into a target region of the patient's body, or to place conductive element 31 in a desired internal body location with minimally invasive techniques, such as catheter or laparoscopic techniques for example. Also, the previously discussed alternative methods of changing polarity, strength, etc., on or between conductive element 31 and terminal 34 may be advantageously used.

The above examples illustrate basic methods of applying a nonuniform, or a relatively uniform, static electric field, to various patient body locations. In all of these examples, the properties of the electric field influencing the patient may be selectively controlled or changed in many ways. As a few examples, the electric field may be:

1. Maintained at a desired field strength level throughout the treatment.
2. Periodically changed from one field strength level to one or more other field strength levels throughout, or changed at any time during, the treatment.
3. Applied for only desired time periods throughout the treatment.
4. Periodically changed from one vector direction, to one or more other vector directions, throughout, or changed at any time during, the treatment.
5. Periodically changed from one polarity to another polarity throughout, or at any time, during the treatment.
6. Periodically applied as a nonuniform field, then as a relatively more uniform field, throughout, or changed at any time during, the treatment.
7. Changed to any combinations of the above at desired time periods throughout the treatment.

Figure 8:
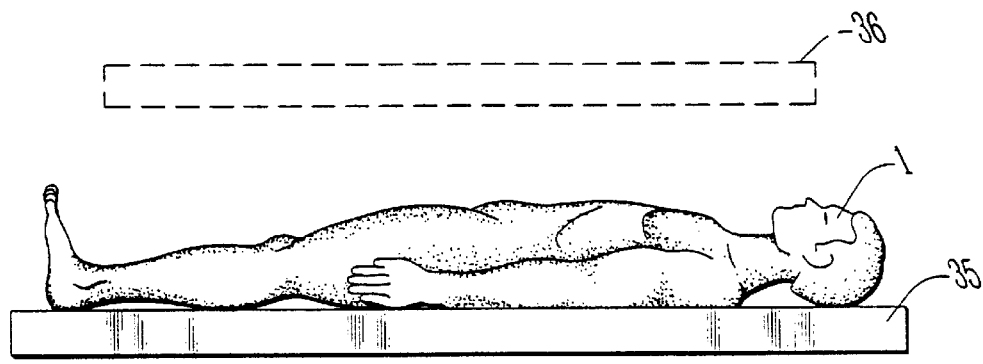
FIG. 8 is a side elevational view showing a patient undergoing total body exposure to a static magnetic field, due to permanently magnetized elements, after receiving a bioactive agent.

FIG. 8 shows an embodiment of a method for exposing all, or large portions, of a patient's body to the influence of a magnetic field produced by permanent magnets. The patient 1 is placed on a treatment element, shown here as treatment pad 35, which contains a plurality of permanently magnetized elements. The magnetized elements are conveniently embedded or maintained in a preferably soft structure providing comfort for the patient. Depending on the field strength and the depth of tissue penetration desired, as well as the direction of the magnetic field vector desired in a particular treatment, the poles of the individual magnetized elements in a particular treatment pad may be placed in an alternating north then south seeking pole arrangement, or in an arrangement with all north and all south poles pointing in the same direction. The poles of the magnetized elements are preferable positioned to face the patient's body, and the magnetic field contribution from each element penetrates the body as the individual fields of the magnetized elements curve (depending on the pole arrangement) toward, or away from, the poles of the adjacent elements.

If desired for a particular treatment method, an additional treatment element, shown here as structure 36, with a plurality of permanently magnetized elements may be positioned on or above the patient. The magnetized elements in this structure may be imbedded in soft material for patient comfort, and also to conform to the patient's body if the structure is to be laid on the body, or the structure may hold the magnetized elements in rigid relationship if the structure is suspended above the patient. The poles of the magnetized elements in structure 36 are preferably positioned to face the poles of the magnetized elements in treatment pad 35, and depending on the pole arrangement desired for a particular treatment, the patient's body would be penetrated by a relatively uniform static magnetic field (for example if the poles facing the patient in treatment pad 35 are all north seeking, and the poles facing the patient in structure 36 are all south seeking), or a nonuniform static magnetic field (for example if the poles facing the patient in both treatment pad 35 and structure 36 are all north seeking). In either case, the strength of the static magnetic field within the patient's body may be adjusted to a desired level by choosing magnetized elements of specific power, or by adjusting the space between treatment pad 35 and structure 36. Also, the strength of the magnetic field within the patient's body may be adjusted by adjusting the position of the patient's body in relationship to treatment pad 35 and structure 36. For example, the patient could be laid on a table, etc., which does not impede the passage of magnetic fields, and structure 35 could be spaced some distance under the table to reduce the magnetic field strength applied to the patient.

Alternatively, structure 36 may contain magnetizable elements instead of magnetized elements.

Additionally, if treatment pad 35 is used without structure 36, treatment pad 35 may be placed at an angle to, instead of parallel with, the patient. Also, if both treatment pad 35 and structure 36 are used, either one or both may be placed at an angle to, instead of parallel with, the patient.

Figure 9:
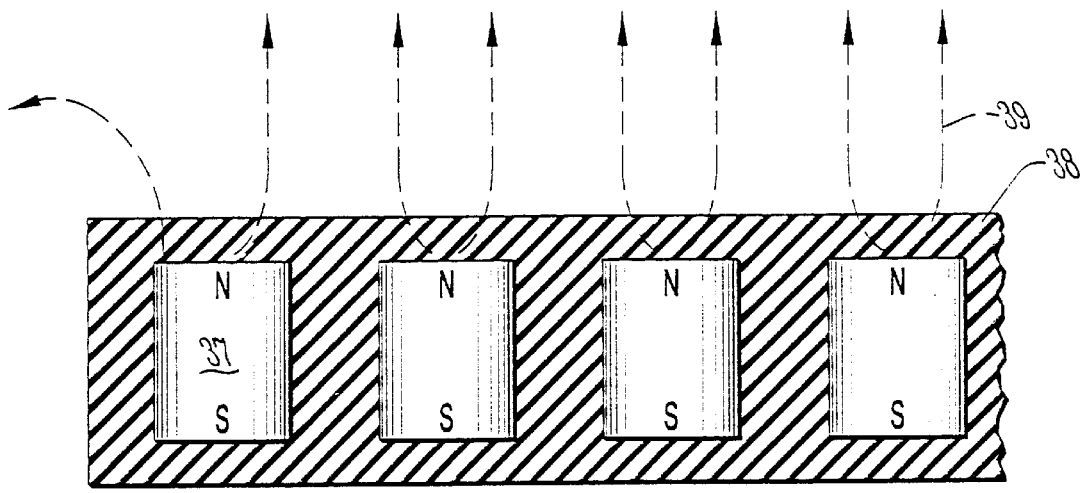
FIG. 9 is a cross-sectional view illustrating a portion of an embodiment of a static magnetic field treatment element which can be used in the arrangement shown in FIG. 8.

FIG. 9 shows a cutaway portion of a treatment pad, such as 35 in FIG. 8, where the magnetized elements 37 are imbedded in a soft material 38 to maintain the relative positions of the magnetized elements and also to provide patient comfort (material 38 may alternately be rigid). Elements 37 may conveniently be permanent magnets such as those supplied by Bunting Magnetics Company, Newton, Kans. for example. The soft imbedding material 38 may be silicone rubber such as that supplied by GE Silicones, Waterford, N.Y. for example. FIG. 9 shows the magnetic elements 37 placed with all north seeking poles facing one direction, and all south seeking poles facing in the opposite direction. In this arrangement, except for around the edges of material 38, the individual magnetic field 39 emanating from the pole of each element 37 repel the individual fields from the poles of adjacent magnetic elements. The individual fields thus do not traverse a short path to terminate on the adjacent magnetic elements, and would create a uniform overall magnetic field penetrating deeply, or completely through, the patient's body depending on the magnetization level of elements 37 and the distance between the elements 37 and the patient's body.

It is noted that permanent magnets may be formed by molding particles of magnetizable material in a desired size and shape, then the molded member or a specific portion of it is magnetized. Permanent magnets may thus be produced with large pole surfaces capable of exposing large areas of the patient's body to a magnetic field from only one or two magnets, and could be used in place of the structure of FIG. 9. Also, magnetizable particles may be calendered into flexible sheets and then magnetized, and such magnetized flexible sheets may be used in place of the structure of FIG. 9 if the lower magnetic field strength produced by such sheets is sufficient for the desired treatment need.

Fabrics or other surfaces such as blankets, etc., may be placed between the soft material 38 and the patient for comfort, and also soft material 38 will conform to the patient's body if it is placed on top of a mattress, etc. The additional magnetic field structure 36 of FIG. 8 may be constructed in the same manner as shown in FIG. 9, and structure 36 may be laid directly on top of the patient. However, more control over the applied magnetic field is achieved (as the patient moves around, etc.) by suspending structure 36 at some desired distance above the patient, and in this instance the magnetic elements 37 may be imbedded in, or attached to, rigid material such as epoxy for example.

Figure 10:
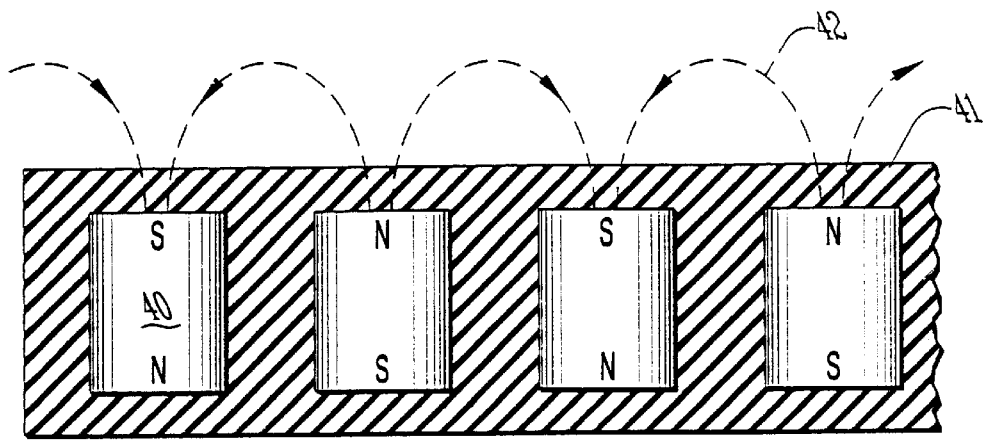
FIG. 10 is a cross-sectional view illustrating a portion of another embodiment of a static magnetic field treatment element which can be used in the arrangement shown in FIG. 8.

FIG. 10 shows a cutaway portion of a treatment pad such as pad 35 in FIG. 8, where the magnetized elements 40 are imbedded in a soft material 41 to maintain the relative position of the magnetized elements and also provide patient comfort (material 41 may alternately be rigid). Magnetized elements 40 may conveniently be permanent magnets, and the soft imbedding material 41 may be silicone rubber. FIG. 10 shows the poles of magnetic elements 40 placed in an alternating north/south seeking pole arrangement. In this arrangement the individual magnetic fields 42 from each element 40 transverse a closed loop with the poles of adjacent elements, and the individual fields 42 penetrate to a depth in the patient's body based on the field strength and spacing of elements 40. The magnetic element arrangement of FIG. 10 would be most useful in exposing the patient 1 to a nonuniform static magnetic field which penetrates and provides strong polarizing force to only a limited depth within the body. It is noted that permanent magnets are currently available with various pole arrangements, such as two or more poles facing in the same direction for example, and these alternate pole arrangements may be used as elements 40.

Figure 11:
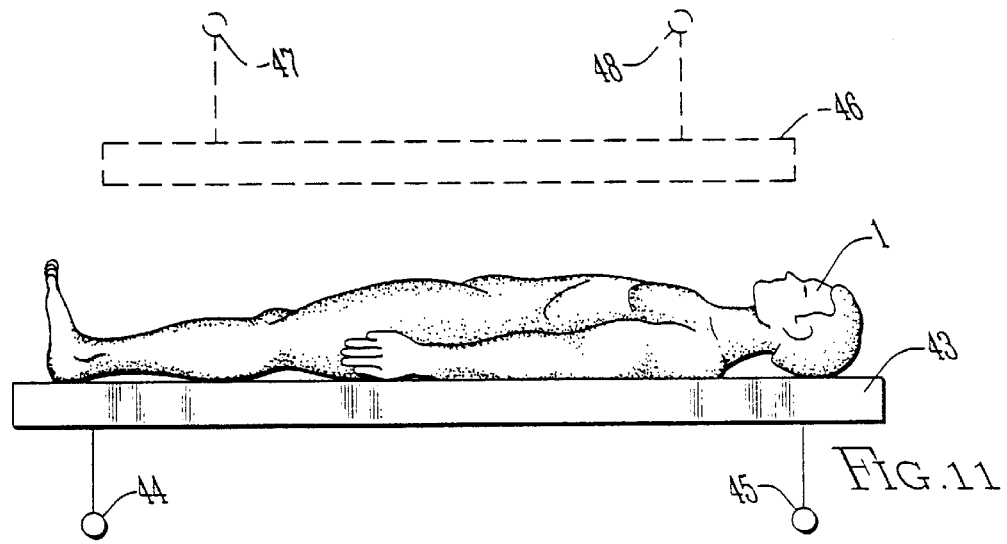
FIG. 11 is a side elevational view showing a patient undergoing total body exposure to a static magnetic field from direct current driven electromagnet elements after receiving a bioactive agent.

FIG. 11 shows an embodiment of a method for exposing all, or a large portion of, a patient's body 1 to the influence of a static magnetic field emanating from direct current electromagnet elements contained in a treatment pad 43 and driven by current from a DC power supply system that is connected to terminals 44 and 45. Such an embodiment will in many cases be preferred over the use of permanent magnetic elements because the properties of the magnetic field, impinging on the patient from treatment pad 43, may be selectively controlled or changed if desired by changing the current applied to terminals 44 and 45 by known timing, switching, and current control methods. For example, treatment pad 43 will expose the patient's body to a nonuniform static magnetic field which can be selectively:

1. Maintained at a desired field strength level throughout the treatment.
2. Periodically changed from one field strength level to one or more other field strength levels throughout, or changed at any time, during the treatment.

3. Applied for only desired time periods throughout the treatment.
4. Periodically changed from one polarity to the other throughout, or changed at any time during, the treatment.
5. Changed in any combination of the above at desired time periods throughout the treatment.

The poles of the electromagnet elements of treatment pad 43 are preferably positioned to face the patient's body, and the coils of the electromagnet elements may be connected so all of the same magnetic poles face in the same direction (such as all north seeking poles for example) for maximum penetration of a strong static magnetic field into the patient's body. Alternately, the electromagnet coils of the elements may be connected so the north pole of one electromagnet element is placed next to the south pole of an adjacent electromagnet element so the field traverses a loop between the elements, thereby limiting the depth of penetration into the patient's body. Also, the depth and strength of field penetration into the patient's body may be controlled by moving treatment pad 43 closer to, or further away from, the body. Also, treatment pad 43 may be placed at an angle to, instead of parallel with, the patient.

As an option, an additional structure 46 of electromagnet elements may be laid on or suspended above the patient and driven through terminals 47 and 48 to work cooperatively with treatment paid 43 or in opposition to it. If the individual magnetic fields produced by the electromagnet elements of structure 46 are of opposite polarity to those produced by the electromagnet elements of treatment pad 43, the field lines connect and the patient's body is exposed to a relatively uniform static magnetic field. Also, structure 46 and/or treatment pad 43 may be placed at an angle to, instead of parallel with, the patent.

Selectively changing the current flow to, and/or the time that the current is applied to, the electromagnet elements of treatment pad 43 and structure 46 may be used to change the magnetic field influence produced between them, and thus through the patient's body. For example:

1. Any, or any combination of, the possible magnetic field changes noted above for treatment pad 43 alone when supplying a nonuniform static magnetic field, may be achieved with the combination of treatment pad 43 and structure 46 supplying a uniform magnetic field.
2. The current flow direction to treatment pad 43 and/or structure 46 may be selectively changed throughout the treatment, or during desired time periods during the treatment, to apply a cooperative uniform static magnetic field to the patient for one period, and then a nonuniform static magnetic field may be applied by driving the treatment pad 43 and the structure 46 in opposition for one or more additional time periods of the treatment.
3. The electromagnet elements of treatment pad 43 and of structure 46 may be activated in combination, or alternately, to expose the patient to first one type or direction of magnetic field influence, then to another type or direction of magnetic field influence for other periods of the treatment time. For example, treatment pad 43 may be activated for a period of time exposing the patient to a nonuniform static magnetic field, and then 46 may also be activated for one or more periods of time to alternately expose the patient to a uniform static magnetic field.

Many other operational variations are possible. Also, it is noted that in some cases it may be desirable for structure 46 to simply be a magnetizable material instead of containing permanent or electromagnet elements. This magnetizable material would attract magnetic field lines from treatment pad 43 to pass through the patient's body, and structure 46 may be smaller than treatment pad 43, thus attracting magnetic field lines from treatment pad 43 more strongly to the region of the body under structure 46.

In most uses of the FIG. 11 method, the patient would be placed on the treatment pad 43, then administered the desired bioactive agent or agents through any desired route, and then at an appropriate point in time treatment pad 43 and/or structure 46 would be activated for some period or some portion of the effective life of the bioactive agent to increase the efficacy of the agent throughout the body.

Figure 12:
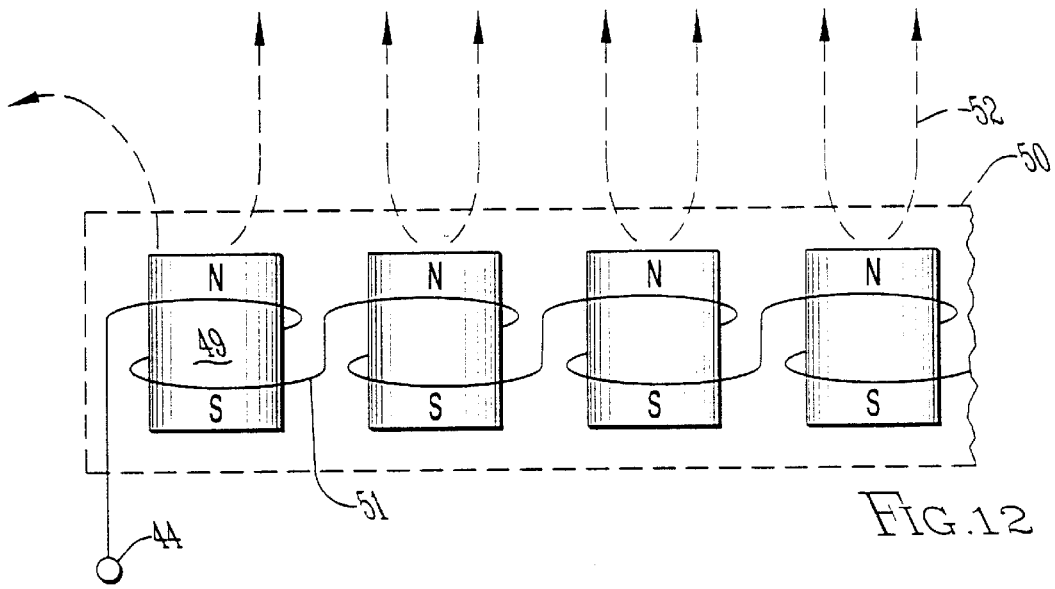
FIG. 12 is a cross-sectional view illustrating a portion of an embodiment of a static magnetic field treatment pad which can be used in the arrangement shown in FIG. 11.

FIG. 12 shows a cutaway portion of a treatment pad such as pad 43 in FIG. 11, where electromagnet elements 49 are imbedded in a soft material 50, such as silicone, to maintain the relative positions of the electromagnet elements and also to provide patient comfort (the material 50 may alternately be a rigid imbedding material such as epoxy for example). The windings of the electromagnet members 49 may be connected so that the same magnetic poles face the patient, as shown. In this connection arrangement, except for areas around the edges of treatment pad 43, the individual static magnetic fields 52 emanating from the pole of each element 49 repel the individual fields from the poles of adjacent electromagnet elements. The individual fields thus do not traverse a short path to terminate on the adjacent electromagnet elements, but instead penetrate deeply, or completely through, the patient's body depending on the magnetic field strength of elements 49 and the distance between the elements 49 and the patient's body.

Fabrics or other surfaces such as blankets, etc., may be placed between soft material 50 and the patient for patient comfort, and also soft material 50 will conform to the patient's body if it is placed on top of a mattress, etc. The additional magnetic field structure 46 of FIG. 11 may be constructed in the same manner as shown in FIG. 12 if the structure 46 is to be laid on the patient. However, more control over the applied field is achieved (as the patient moves around, etc.) by suspending structure 46 at some desired distance above the patient, and in this instance the electromagnet elements 49 may be imbedded in, or attached to, a rigid material such as epoxy for example.

It is also noted that the invention contemplates methods in which one or the other of treatment pad 43 and structure 46 in FIG. 11 contains permanent magnetic elements, while the other contains electromagnet elements, and/or that either treatment pad 43 or structure 46 may contain both permanent and electromagnet elements so the field emanating to the patient may be altered in pattern or strength by application of current to the electromagnet elements.

It is also contemplated that the invention includes methods in which both static magnetic and static electric elements are used together in one or more treatment elements to simultaneously or individually supply static magnetic and/or static electric fields.

Methods of applying properly sized and/or shaped treatment pads or other items containing permanent magnetic and/or electromagnetic elements to only a desired region of the patient's body will be readily apparent in light of the discussion of FIG. 6 and FIG. 7, and that discussion will not be repeated here other than to note that magnetic elements may be used in place of the charged conductive elements of FIG. 6 and FIG. 7, or a combination of magnetic elements and charged conductive elements may be used, for exposing only a desired region of the patient's body to a magnetic, or magnetic and electric, polarizing field to increase the effectiveness of an administered bioactive agent.

Figure 13:
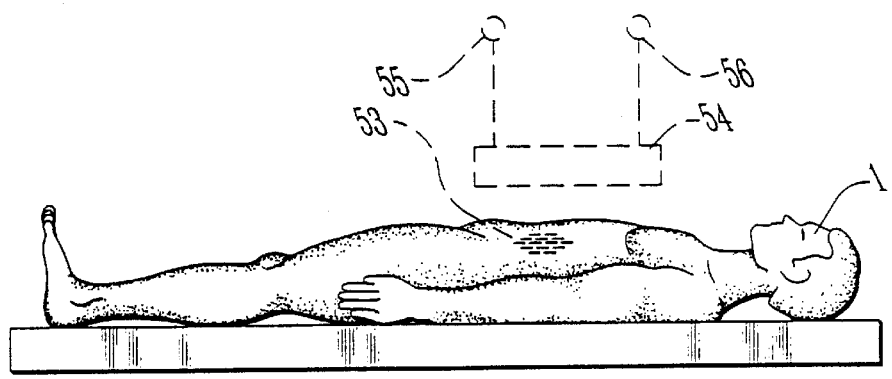
FIG. 13 is a side elevational view showing a patient who has received a bioactive agent and who is being exposed to a static magnetic field at a target region where magnetic, or magnetizable, material has been applied.

FIG. 13 shows a preferred embodiment of a method of applying a magnetic field to only a desired internal region of a patient's body 1. Magnetic microparticles 53 may be injected, or otherwise placed, into a target region of the patient's body (for example into a disease site) so that a bioactive agent administered to the body gains increased efficacy from exposure to the magnetic field only in the target region of the body. Alternately, microparticles 53 may be magnetizable materials, such as paramagnetic, feromagnetic, or dimagnetic materials (from Bangs Laboratories, Carmel, Ind., for example), for example, which become magnetic only when they are exposed to magnetic fields, and thus would increase efficacy of the bioactive agents in the target site only during this period. Magnetic fields from another source, such as structure 54 in FIG. 13, would cause the magnetizable materials to become magnets only while current is applied to terminals 55 and 56 of structure 54, and the time magnetized, strength, direction, and polarity of the static magnetic field of microparticles 53 would be controlled by structure 54.

While microparticles 53 are shown in FIG. 13, larger magnetic or magnetizable treatment elements could be used instead. One or more of such larger treatment elements can be surgically implanted or inserted into a body cavity so as to bring the magnetic treatment element or elements as close as possible to the body target region for maximum effect, and also to aid in continuing the effect to only the target region.

As an additional example of a method of applying a uniform static magnetic field to all, or a portion of, a patient's body, the patient, or a desired portion of the patient's body, may be placed inside of a direct current conducting coil. Passage of current through such a coil creates a dense, uniform magnetic field through the core of the coil, and thus through the region of the patient's body within the coil. The time the static magnetic field is applied, the direction of the field, and the strength of the field would be controlled by known current control, switching, and timing methods.

It is noted that methods of directing, terminating, or shielding both static electric and static magnetic fields are known by those skilled in the art, and that the invention contemplates advantageously using these methods with the invention in desired situations. For example, in a treatment exposing external portions of the body to static electric fields, a conductive shield can be used to intercept the fields before they contact portions of the body not intended to be treated. Also, a conductive shield may be used to cover a portion of any treatment element inserted into the body to allow static electric fields to be emanated from the treatment element only in a desired area. Similar methods, using ferrous or other magnetic field terminating materials, can also be used for magnetic treatments and elements.

The particular methods and equipment by which the invention can best be used in a particular treatment situation will depend on factors such as the bioactive agent administered, the malady or condition to be treated, and the desired body region of the treatment. As a simplified example of one preferred method for a particular situation, consider the treatment of a breast cancer tumor in the upper-outer quadrant of a female breast. Assume that the tumor is discovered early and is very small, and that the decision is made to surgically remove just the tumor (instead of the entire breast) and to then treat the breast with at least one chemotherapeutic agent, such as adriamycin, to try to destroy any remaining but undetectable cancer cells in the area. Adriamycin, like most bioactive agents for treatment of neoplastic disease, is toxic enough to require intravenous injection over at least a 30 minute period to control the blood concentration levels. Also, like most cancer treatment agents, adriamycin acts against any rapidly proliferating cell of the body, such as certain cells in bone marrow, the intestinal mucosa, testis, and hair follicles as well as cancer cells. In addition, like most cancer treatment agents, adriamycin has a relatively short half-life, losing up to 50% of it's potency within 2 hours of administration, followed by a slower potency loss of an additional 30% within 15 to 20 hours of administration. A typical dose schedule of adriamycin for breast carcinoma is a 30 minute i.v. injection, on each of three days, repeated every three or four weeks. Methods of the invention can be used in several ways to influence the treatment.

Continuing with the above example, the standard adriamycin treatment dose and schedule would be administered with a portable polarizing field (either electric or magnetic) treatment pad such as the treatment pad 27 shown in FIG. 6 adhered to each breast before beginning each injection, but with the treatment pad deactivated. Approximately 10 minutes after starting the injection, after the adriamycin has had time for distribution into the breasts, the treatment pad would be activated to expose the breasts to polarizing fields to increase the efficacy of the adriamycin against cancer cells in the breast area. The treatment pads would remain activated for 8 hours following each injection to ensure that the applied polarizing fields were acting upon the target tissue only while sufficient levels of adriamycin are present for maximum reaction with any cancer cells. The treatment pads would then be deactivated and removed after 8 hours to avoid exposing the breasts to polarizing fields while only low levels of adriamycin are present. In this method, only the breast area of the patient would be exposed to the increased potency of the adriamycin/polarizing field combination, and the increased potency in the breast area would enhance the possibility of successful treatment.

Additionally, the decision may be made to also treat the lymph nodes under the arm adjacent to the breast since normal lymphatic drainage out of the breast occurs to these nodes, and any cancer cells leaving the breast will likely be at least temporarily trapped in this area. In this case an additional treatment element may be applied under the arm to expose the lymph nodes to polarizing fields during the treatment period.

The above noted specific suppliers, materials, methods, and embodiments of the invention have been detailed simply to help illustrate and describe the invention, and are not intended to be exhaustive or to limit the invention to the precise form or methods disclosed. Many modifications and variations will be apparent to an ordinarily skilled person in light of the above teaching, and it is intended that such modifications and variations be included in the scope of the invention.

What I claim is:

1. A method of treating a person's body having a disease condition, the disease condition responding to a least some degree to treatment with a therapeutic agent, the therapeutic agent being nonmagnetic and biologically active against the disease condition for a period of time, the method comprising the steps of:

(a) administering the therapeutic agent to the person's body; and (b) exposing at least a portion of the person's body to a polarizing static field for at least a portion of the time that the therapeutic agent is biologically active against the disease condition, wherein the efficacy of the therapeutic agent is increased due to the presence of the static field.

2. The method of claim 1, wherein said step (b) further comprises the step of varying strength of the polarizing static field, such that the polarizing static field remains at a substantially constant strength for a plurality of seconds before varying.

3. The method of claim 1, wherein said step (b) further comprises the step of varying direction of the polarizing static field, such that the polarizing static field remains at a substantially constant direction for a plurality of seconds before varying.

4. The method of claim 1, wherein said step (b) further comprises the step of changing polarity of the polarizing static field, such that the polarizing static field remains at a substantially constant polarity for a plurality of seconds before changing.

5. The method of claim 1, wherein said step (b) further comprises the step of alternately applying and removing the polarizing static field, such that the field remains substantially applied for a plurality of seconds before being removed.

6. The method of claim 1, further comprising the step of shielding at least one selected portion of the person's body from exposure to the polarizing static field.

7. The method of claim 1, wherein the polarizing static field comprises an electrostatic field.

8. The method of claim 7, wherein said step (b) further comprises the step of alternately applying and removing the electrostatic field, such that the electrostatic field remains substantially applied for a plurality of seconds before being removed.

9. The method of claim 7, further comprising the step of shielding at least one selected portion of the person's body from exposure to the electrostatic field.

10. The method of claim 7, wherein said step (b) further comprises the step of varying strength of the electrostatic field, such that the electrostatic field remains at a substantially constant strength for a plurality of seconds before varying.

11. The method of claim 7, wherein said step (b) further comprises the step of varying direction of the electrostatic field, such that the electrostatic field remains at a substantially constant direction for a plurality of seconds before varying.

12. The method of claim 7, wherein said step (b) further comprises the step of changing polarity of the electrostatic field, such that the electrostatic field remains at a substantially constant polarity for a plurality of seconds before changing.

13. The method of claim 1, wherein the polarizing static field comprises a magnetostatic field.

14. The method of claim 13, wherein said step (b) further comprises the step of alternately applying and removing the magnetostatic field, such that the magnetostatic field remains substantially applied for a plurality of seconds before being removed.

15. The method of claim 13, further comprising the step of shielding at least one selected portion of the person's body from exposure to the magnetostatic field.

16. The method of claim 13, wherein said step (b) further comprises the step of varying strength of the magnetostatic field, such that the magnetostatic field remains at a substantially constant strength for a plurality of seconds before varying.

17. The method of claim 13, wherein said step (b) further comprises the step of varying direction of the magnetostatic field, such that the magnetostatic field remains at a substantially constant direction for a plurality of seconds before varying.

18. The method of claim 13, wherein said step (b) further comprises the step of changing polarity of the magnetostatic field, such that the magnetostatic field remains at a substantially constant polarity for a plurality of seconds before changing.

19. The method of claim 13, wherein said step (b) further comprises the steps of:

actuating a magnetic element;

including the magnetic element in a treatment element; and placing the treatment element in a location such that the portion of the person's body is exposed to a magnetostatic field generated by the magnetic element.

20. The method of claim 19, wherein the magnetic element comprises a permanently magnetized element having magnetic poles.

21. The method of claim 20, wherein the treatment element comprises a plurality of treatment elements, and at least one of the plurality of treatment elements comprises a magnetizable element.

22. The method of claim 19, wherein the magnetic element is an electromagnet element generating magnetostatic fields.

23. The method of claim 22, wherein:

the treatment element comprises a plurality of treatment elements, at least one of the plurality of treatment elements comprises an electromagnet element for generating magnetostatic fields, and at least one other of the plurality of treatment elements comprises a magnetizable element.

24. The method of claim 23, wherein said step (b) further comprises the step of varying direction of the magnetostatic field, such that the magnetostatic field remains at a substantially constant direction for a plurality of seconds before varying.

25. The method of claim 23, wherein said step (b) further comprises the step of changing polarity of the magnetostatic field, such that the magnetostatic field remains at substantially constant polarity for a plurality of seconds before changing.

26. A method of treating a person's body having cancer, the cancer responding to at least some degree to treatment with a chemotherapeutic agent, the chemotherapeutic agent being nonmagnetic and biologically active against the cancer for a period of time, the method comprising the steps of:

(a) administering the chemotherapeutic agent to the person's body; and (b) exposing at least a portion of the person's body to a polarizing static field for at least a portion of time that the chemotherapeutic agent is biologically active against the cancer, wherein the efficacy of the chemotherapeutic agent is increased due to the presence of the static field.

27. The method of claim 26 wherein said chemotherapeutic agent is adriamycin.

* * * * *